United States Patent [19]

Agback et al.

[11] Patent Number: 5,302,718

[45] Date of Patent: Apr. 12, 1994

[54] COMPOUNDS CONTAINING AN AMINO SALICYLIC ACID MOIETY LINKED TO A SULPHAPYRIDINE MOIETY VIA STABLE BRIDGE

[75] Inventors: Hubert Agback, Uppsala; Leif Ahrgren, Örbyhus; Thomas Berglindh, Uppsala; Martin Haraldsson, Vallentuna; Göran Smedegard, Uppsala; Lars-Inge Olsson, Södertälje, all of Sweden

[73] Assignee: Kabi Pharmacia AB, Uppsala, Sweden

[21] Appl. No.: 973,753

[22] Filed: Nov. 9, 1992

[30] Foreign Application Priority Data

Nov. 18, 1991 [SE]  Sweden .............................. 9103397-7

[51] Int. Cl.$^5$ .................. C07D 237/26; C07D 211/56; C07D 249/12
[52] U.S. Cl. .................... 544/235; 544/283; 544/292; 544/297; 544/336; 544/349; 546/159; 546/157; 546/221; 546/304; 546/233; 546/312; 548/121; 548/127; 548/128; 548/130; 548/131; 548/133; 548/135; 548/138; 548/143; 548/161; 548/194; 548/222; 548/234; 548/241; 548/332.5; 548/245; 548/264.8; 548/372.1; 548/362.1; 548/307.4
[58] Field of Search ............... 546/312, 304, 159, 157, 546/221, 223; 544/235, 283, 292, 297, 336, 349; 548/121, 127, 128, 130, 131, 133, 135, 138, 143, 161, 194, 222, 234, 241, 351, 372, 375, 248, 264.8, 326, 338

[56] References Cited

U.S. PATENT DOCUMENTS

| 2,396,145 | 3/1946 | Askelof | 534/664 |
| 3,915,951 | 10/1975 | Agback | 534/664 |
| 4,663,334 | 5/1987 | Carson | 546/312 |
| 4,897,397 | 1/1990 | Shih et al. | 546/312 |

OTHER PUBLICATIONS

T. Pullar; Br. J. Clin. Pharmacol, vol. 30, pp. 501-510 (1990).

S. Pacneco, K. Hiller, C. L. Smith, Brazttian J. Med Biol Res, vol. 23, pp. 1323-1334 (1990).

C. Astbury, J. Hill J R. Lowe, D. Campbell, H. A. Bird, Bird, British J. Rneumatology vol. 29, pp. 465-467 (1990).

T. Roitt, J. Broscott, D. Male; Immunology 2nd ed 1989.

Primary Examiner—C. Warren Ivy
Assistant Examiner—Raymond Covington
Attorney, Agent, or Firm—Fred Philpitt

[57] ABSTRACT

A compound of the formula Het—NR—SO$_2$—Ph-$^2$—A—Ph$^1$(COOH)(OH) and tautomeric form, salts, solvates, C$_{1-6}$ alkyl esters and pharmaceutical compositions of the compound. Ph$^1$ and Ph$^2$ are benzene rings with the proviso that carboxy and hydroxy are ortho to one another. Het includes an optionally substituted heterocyclic ring which includes conjugated double bonds and binds to nitrogen in NR. The compound is characterized in that A is a bridge which is stable against reduction because it is not azo, and in that R is hydrogen or lower alkyl.

The invention also includes the preparation of the compound and its use as a drug, particularly for treating autoimmune diseases.

20 Claims, No Drawings

COMPOUNDS CONTAINING AN AMINO SALICYLIC ACID MOIETY LINKED TO A SULPHAPYRIDINE MOIETY VIA STABLE BRIDGE

It has long been known that compounds which include a salicylic acid structure coupled by a reductive cleavable bridge —N=N— (=—A—) to a ring position in a benzenesulphonic acid which, in turn, is amidated at the amine group of an amine-substituted heterocyclic ring which includes conjugated double bonds can exhibit a therapeutic effect against ulterative colitis, rheumatoid arthritis and other diseases that are considered to be autoimmune. See for instance Askelöf et al, U.S. Pat. No. 2,396,145, Agback and Lindblom, U.S. Pat. No. 3 915 951, T. Pullar. Br. J. Clin. Pharmacol., vol. 30, pages 501-510 (1990), I. G. Tumanova, Ia A. Sigidin: Ter-Arkh., vol. 59, pages 80-83 (1987), S. Pacheco, K. Hillier, C. L. Smith, Brazilian J. Med. Biol. Res., vol. 23, pages 1323-34 (1990) and C. Astbury, J. Hill, J. R. Lowe, D. Campbell, H. A. Bird, British J. Rheumatology, vol. 29, pages 465-467 (1990). Autoimmune diseases are described and exemplified by, inter alia, I. Roitt, J. Brostoff, D. Male: Immunology, 2nd ed., 1989.

The best known compound possessing the aforesaid therapeutic effect is sulfasalazine. Although analogues of sulfasalazine have been described, none has yet resulted in an accepted drug.

Sulfasalazine is clinically effective in the treatment of autoimmune diseases, such as for instance rheumatoid arthritis, ulterative colitis, ankylosis spondylitis, reactive arthritis, psoriasis and psoriasis arthritis. See for instance D. R. Porter and H. A. Capell: Bailliers Clin. Rheumatol., vol. 4, pages 535-551 (1990), M. B. Ferraz, P. Tugwell, C. H. Goldsmith and E. Atra: J. Rheumatol., vol. 17, pages 1482-1486 (1990), A. K. Gupta, C. N. Ellis, M. T. Siegel, E. A. Duell, C. E. M. Griffiths, T. A. Hamilton, B. J. Nickoloff and J. J. Voorhees: Arch. Dermatol, vol. 126, pages 487-493 (1990), G. Watkinson: Drugs, vol. 32: suppl. 1, pages 1-11 (1986).

The drugs mostly prescribed in the treatment of rheumatoid arthritis are the antiinflammatory drugs, so-called NSAIDs (Nonsteroidal Anti-Inflammatory Drugs). These drugs are considered to act against the symptoms of the disease. On the other hand, sulfasalazine is classified as a disease-modifying drug. Also belonging to the same group of drugs are gold salt, penicillamine, chloroquine and the immunosuppressive drugs methotrexate, azathioprine and cyclophosphamide, all having radically divergent structures.

A number of pharmalogical model systems are available for evaluating drugs which are potentially usable for the treatment of autoimmune diseases. One of the most important properties of the NSAIDs in such model systems is their ability to inhibit prostaglandin synthesis and therewith associated biological effects.

Sulfasalazine deviates radically from the active pattern of NSAIDs in such model systems, both clinically and experimentally. Sulfasalazine has been characterized in a number of models judged to be relevant to describe the disease-modifying effective component. For example, it has been shown that the activation of immunocompetent and inflammatory cells are influenced by salphasalazine because it inhibits activation and proliferation of T-lymphocytes and also activation of granulocytes and liberation of mediators.

The clinical effect of sulfasalazine when treating ulterative colitis has been attributed to 5-aminosalicylic acid, which is formed by reductive cleaving of the mother molecule in the colon. Sulfapyridine is formed at the same time. When treating other autoimmune diseases, such as rheumatoid arthritis for instance, the effective component has been considered to be the intact sulfasalazine molecule or released sulfapyridine or, most probably, both components. The secondary effects of sulfasalazine have essentially been considered to be related to liberated sulfapyridine.

We have now discovered a novel type of analogues to sulfasalazine which exhibit good biological availability and effects in models used in studying autoimmune diseases, such as rheumatoid arthritis and ulterative colitis for instance. The analogues have the aforedescribed structure, but with the azo group (A) replaced with a bridge which is stable against hydrolysis and/or reduction in vivo, for instance in the colon. Such compounds are novel. Thus, in its broadest concept, the invention includes compounds of the structure I $$\text{Het}-\text{NR}-\text{SO}_2-\text{Ph}^1-\text{A}-\text{Ph}^2(\text{COOH})(\text{OH}) \qquad \text{I}$$

and tautomeric forms, salts and solvates, and optionally alkyl esters with 1-6 carbon atoms in the carboxyl group.

In the above structure I, Het is a heterocyclic ring according to the aforegoing; $Ph^1$ is a benzene ring; $Ph^2$ (COOH)(OH) is a benzene ring with carboxy and hydroxy ortho to one another; R is hydrogen or a lower alkyl ($C_{1-6}$). Het, $Ph^1$, $Ph^2$ (COOH)(OH) and the bridge A may be substituted.

The compounds are characterized in that A is a bridge which is stable against hydrolysis and/or reduction in biological systems. A is preferably a straight carbon chain having at most three carbon atoms (—C—C—C—) which includes a carbon-carbon single, double or triple bond, optionally together with an oxo-substituent (=O) on one of the carbon atoms in the chain. By stable against hydrolysis and/or reduction is meant that A lacks a nitrogen-nitrogen bond, such as azo, and optionally also hydrolysis labile ester and amide bonds as a linking structure between $Ph^1$ and $Ph^2$.

In specific embodiments, $Ph^1 = 1,4$ - or 1,3-substituted benzene and $Ph^2$ (COOH)(OH) is an ortho-carboxy-hydroxy substituted phenyl, which may optionally be further substituted with halogen or lower alkyl ($C_1$-$C_6$), preferably methyl, in its 3,4 or 6 position. —A— is —C≡C—, —CH=CH—, —CH$_2$CH$_2$—, —CO—CH=CH—, —CH=CHCO—, —CH$_2$CO—.

In specific embodiments of the inventive compounds, the heterocyclic ring in Het is five-membered or six-membered having two and three conjugated double bonds respectively. The heterocyclic ring in Het may be included in a monocyclic or bicyclic structure. Preferably, ($R_1$, $R_2$, $R_3$)—Het'—Het— is where Het'— is

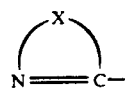

wherein the free valency in

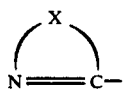

binds to NR;

and X is:

(i) —N=CH—NH—, —N=CH—S—, —N=CH—O—, —NH—N=CH, —O—CH=CH—, —CH=CH—O—, —NH—CH=CH—, —CH=CH—NH—, —CH=CH—S—, —CH=N—NH—, or (ii) —CH=CH—CH=CH—, —CH=CH—CH=N—, —Ch=N—CH=CH—, —CH=CH—N=CH—, —N=CH—CH=CH—, wherein mutually adjacent hydrogen atoms shown in bold (H) can be substituted in pairs with —CH=CH—CH=M—, so as to form a bicyclic structure.

R is hydrogen or lower alkyl ($C_{1-6}$), preferably hydrogen or methyl.

$R_1$, $R_2$, $R_3$ are substituents on carbon atoms in Het'. The groups may be hydrogen, lower alkyl ($C_{1-6}$), halogen, hydroxy, cyano, carboxy, lower alkoxy ($C_{16}$), benzyloxy, lower acyl ($C_{1-7}$), including acetyl, benzoyl, phenyl, benzyl, etc., wherein any benzene rings that occur may be substituted.

Throughout the descriptive part and the Claims of this specification, by lower alkyl and lower acyl is meant groups which contain 1-6 and 1-7 carbon atoms respectively, optionally with substituents of the aforesaid kind.

A is —C≡C—, optionally lower alkyl substituted trans or cis-CH=CH—, —CH$_2$—CH$_2$—, —CO—CH=CH—, —CH=CH—CO—, —CO—, —CH$_2$—CO—, —CH$_2$—, preferably —C≡C— or trans-CH=CH—;

Ph$^2$ is $C_6H_2R_4$, where $R_4$ is hydrogen, halogen or lower alkyl, preferably hydrogen or methyl; and tautomeric forms thereof and salts with alkali metals, preferably sodium, with calcium or magnesium, or with pharmaceutically acceptable amines, such as crystal solvates which include pharmaceutically acceptable solvents, such as water, acetone and ethanol for instance, and also pharmaceutical compositions thereof.

The invention also relates to the use of the compound as a drug, primarily for treating autoimmune diseases in analogy with the use of sulfasalazine and potentially also other inflammatory conditions. Other aspects of the invention include the preparation of the compounds and the production of pharmaceutical compositions containing said compounds and intended for the medicinal indications mentioned below.

The inventive compounds have an immunomodulating effect in biological systems, for instance by inhibiting immunocompetent and inflammatory cell activation and in their pharmacological profile are similar to sulfasalazine but are often more active. Consequently, the inventive compounds are potential drugs for treating such autoimmune diseases as rheumatoid arthritis, ulterative colitis, ankylosing spondylitis, reactive arthritis, psoriasis, psoriasis arthritis, Morbus Crohn, multiple sclerosis, type 1 diabetes, scleroderma, myasthenia gravis, Sjögrens syndrome, systematic lupus erythematosus and chronic asthma. The inventive compounds can also be used conceivably for treating other diseases, particularly those diseases which have an immunological component, irrespective of whether the compounds are known for this medicinal science or not.

Because the novel compounds are unable to form sulfapyridine or any other toxic analog thereof, due to the particular nature of said compounds, it is extremely probable that said compounds lack the side effects due to free sulfapyridine. Our experiments have shown that the biological availability of laboratory animals is often much greater for the inventive compounds than for sulfasalazine and its analogues.

In summary, the novel compounds should prove highly beneficial as drugs for the treatment of autoimmune diseases. The novel inventive compounds can be produced in several ways.

One method involves reacting compound II with compound III.

where R, $R_1$, $R_2$, $R_3$, $R_4$, Ph$^1$ and Het' are the same as above, $R_5$ is hydrogen or preferably lower alkyl having at most six carbon atoms, and X and Y pairwise are —C≡CH and $Z_1$—; —$Z_1$ and HC≡C; —CH=CH$_2$ and $Z_1$—; —$Z_1$ and —CH=CH$_2$; —CO—CH$_3$ and HCO—; —COH and CH$_3$—CO—; —CH$_2$COZ$_2$ and H—; —CHO and Z$_3$CH$_2$—; —CH$_2$Z$_3$ and HCO—; wherein $Z_1$ is bromo or iodo, $Z_2$ is halo, preferably chloro, and $Z_3$ is the residue of a phosphororganic compound of the Wittig type, for instance a triphenyl phosphonium group or a dialkyl phosphonate group.

The compounds II and III are coupled together in a known manner, whereafter when $R_5$ is a lower alkyl, the coupling product is hydrolyzed, preferably in the presence of alkali metal hydroxide, whereafter the product is acidified and then isolated.

When X and Y are —C≡CH and $Z_1$ or $Z_1$ and HC≡C—, the aforesaid coupling process is preferably effected by means of the so-called Heck's reaction, implying catalysis of a palladium compound and a copper compound in the presence of a base and a solvent Suitable palladium compounds are dichlorobis(triphenylphosphine)palladium, dichlorobis[tris(2-methylphenyl)]palladium or tetrakis(triphenylphosphine)palladium. A suitable palladium compound may optionally be prepared in situ, by using, e.g., palladium chloride or palladium acetate together with triphenylphosphine, tris(2-methylphenyl) phosphine or 1,3-bis(diphenylphosphino) propane, etc. Suitable copper compounds are copper (1) iodide or copper (I) bromide. Suitable bases are amines, preferably tertiary amities, such as, for instance, triethylamine or tributylamine or other inorganic or organic bases such as, for instance, sodium hydrocarbonate or sodium acetate. Suitable solvents are, for instance, N,N-dimethylacetamide, N,N-dimethylformamide, ethanol, acetone, tetrahydrofuran, dioxane, toluene, etc., preferably N,N-dimethylacetamide.

When X and Y are —CH=CH$_2$ and $Z_1$ or $Z_1$ and —CH=CH$_2$, the aforesaid coupling is preferably effected by means of the so-called Heck's reaction, implying catalysis of a palladium compound in the presence of a base and solvent. Suitable palladium compounds are divalent inorganic or organic salts of palladium, e.g. palladium (II) chloride and palladium (II) acetate. The salts may optionally be stabilized with customary ligands such as, for instance, triphenylphosphine in the form, for instance, of dichlorobis(triphenylphosphine) palladium. Alternatively, a 0-valence palladium compound can be used such as, for instance, bis(dibenzylidene acetone)palladium or tetrakis(triphenylphosphine)palladium. Suitable bases are tertiary amines such as, for instance, triethylamine or inorganic bases such as sodium hydrogen carbonate or sodium acetate. Suitable solvents are, for instance, N,N-dimethylacetamide, N,N-dimethylformamide, toluene, tetrahydrofuran, dioxane, acetone, etc.

Although the compound of formula $(R_1,R_2,R_3)$—Het'—NR—$SO_2$—$Ph^1$—X, where X is ethenyl, can be produced in several ways, each known per se, the compound is preferably produced by reacting a compound of the formula $(R_1,R_2, R_3)$—Het'—N-R—$SO_2$—$Ph^1$—X, where X is bromo or iodo, with ethylene in the presence of a catalytic quantity of a palladium compound, a base and a solvent, where catalysts and solvents are of a similar type to those used in the reaction between H and III. Another method involves partially reducing a corresponding ethynyl compound with gaseous hydrogen in the presence of a catalyst appropriate for this purpose.

The compound of the formula II, where X is bromine or iodine, is produced in a known manner, for instance by reacting corresponding halogen benzene sulfonyl chloride with corresponding heterocyclic amine in the presence of a base, for instance pyridine or the heterocyclic amine in excess.

When X and Y in formula II and III respective are —CO—$CH_3$ and HCO— or —CHO and $CH_3$—CO—, the aforesaid coupling is effected in a known manner, in the presence of a solvent and a basic or acid condensation agent Suitable bases are, for instance, sodium hydroxide or potassium hydroxide. Suitable acids are strong mineral acids, such as hydrochloric acid or sulphuric acid. Suitable solvents are water, lower alcohols or mixtures thereof. The compound of formula U, where —X is —CO—$CH_3$ or —CHO is prepared in a known manner, for instance by reacting corresponding formylbenzene sulfonyl chloride or acetylbenzene sulfonyl chloride with corresponding heterocyclic amine, in the presence of a base, for instance pyridine or the heterocyclic amine in excess.

When —X and Y— in compound II and HI respectively are —$CH_2COZ_2$ and H—, the reaction is effected in a known manner under Fridel-Craft's conditions, in the presence of a Lewis acid, preferably aluminium chloride in an inert solvent, such as chlorinated hydrocarbon for instance. The compound III, where —X is —$CH_2COZ_2$, is prepared in a known manner, for instance by reacting corresponding alkoxycarbonylbenzenesulfonyl chloride with corresponding heterocyclic amine in the presence of a base, for instance pyridine or the heterocyclic amine in excess, whereafter the intermediary amine is hydrolyzed to corresponding carbonic acid and the acid is halogenated in a known manner, for instance by reacting with thionylchloride or a phosphorous halogenide.

Another method is by reacting a compound of formula IV with a compound of formula V

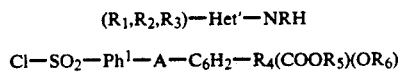$(R_1,R_2,R_3)$—Het'—NRH      IV

Cl—$SO_2$—$Ph^1$—A—$C_6H_2$—$R_4(COOR_5)(OR_6)$      V where Het', $Rh^1$, R, $R_1$, $R_2$, $R_3$, $R_4$ and $R_5$ have the same significance as above and $R_6$ is a lower acyl, preferably acetyl or the residue of an aliphatic or aromatic sulfonic acid, preferably methyl sulfonyl or p-toluenesulfonyl; in the presence of a basic condensation agent and a solvent, wherein the basic condensation agent may be the compound IV in excess or preferably an organic base, for instance pyridine, whereafter the resultant intermediary compound is subjected to base-catalyzed hydrolysis, preferably by reaction with alkali metal hydroxide in water.

The aforesaid compound of formula V is produced in a known manner, by reacting corresponding sulfonic acid or its alkali metal sulfonate with a suitable chlorinating agent, preferably thionylchloride in the presence of N,N-dimethylformamide. The sulfonic acid is produced in a known manner according to any one of the abovementioned general methods, preferably by converting corresponding ethynyl or ethenyl aryl compound with an aryliodide or arylbromide. A third method of producing a compound according to the invention is by transforming the bridge A in an inventive compound or its intermediate having the formula VI (below) to another bridge in a known manner, optionally with subsequent transformation of the intermediate to the final compound.

One example of such methods involves the addition of water to a compound of formula VI

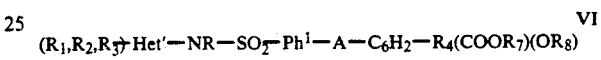$(R_1,R_2,R_3)$—Het'—NR—$SO_2$—$Ph^1$—A—$C_6H_2$—$R_4(COOR_7)(OR_8)$      VI where R, $R_1$, $R_2$, $R_3$, Het', $Ph^1$, $R_4$ are the same as above, $R_7$ is hydrogen or $R_5$, where $R_5$ is the same as above, $R_8$ is hydrogen or $R_6$, where $R_6$ has the same meaning as above, and —A— is —C≡C—. The resultant compound has the formula VI with A=—$CH_2CO$—. Addition of water to the triple bond takes place in the presence of a mineral acid or a strong organic acid, preferably formic acid, optionally in the presence of metal salts of, e.g., mercury or palladium, with subsequent alkaline hydrolysis when $R_7$ and/or $R_8$ are not hydrogen. Another method is to reduce the compound of formula VI, where R, $R_1$, $R_2$, $R_3$, Het', $Ph^1$, $R_4$, $R_7$ and $R_8$ are the same as above and —A— is —$CH_2CO$ to a corresponding compound in which —A— is —$CH_2$-CHOH—, and by then converting this compound with mineral acid so as to eliminate water and form a compound where —A— is —CH=CH— with subsequent alkaline hydrolysis when $R_7$ and/or $R_8$ are not hydrogen.

A third method is to reduce a compound of formula VI, where R, $R_1$, $R_2$, $R_3$, Het', $Ph^1$, $R_4$, $R_7$ and $R_8$ are the same as above and —A—is —C≡C— or —CH=M— to a corresponding compound in which —A— is —$CH_2CH_2$— by means of catalytic hydrogenation in a known manner, followed by alkaline hydrolysis when $R_7$ and/or $R_8$ are not hydrogen. When the inventive compound is a salt, the compound is produced, for instance, by first producing a corresponding acid and then reacting this acid with a corresponding salt former, for instance in the form of a metal hydroxide or organic amine, in the presence of a solvent, preferably water or a mixture of water and one or more organic solvents, or optionally solely in the presence of an organic solvent When the salt is not readily soluble in the solvent used, the salt is preferably allowed to crystalize from the solvent and is isolated by filtration or some similar process. When the not readily dissolved salt is an alkali metal salt, preferably sodium or potassium, the final hydrolysis applied to remove any protective groups may be carried out so that the synthesis mixture will be neutralized and the desired salt is crystallized directly from the mixture. If the salt is relatively soluble in the solvent used, the salt is preferably produced by reacting equimolar quantities, whereafter the solvent is removed by evaporation.

It is possible in some instances for a compound to form a distinct solvate with a solvent Such solvates, which contain pronounced quantities of solvent, are also included by the invention when the solvents used are pharmaceutically acceptable, such as water, acetone and ethanol for instance. Such a solvate is produced by crystallization from the solvent concerned, optionally in mixture with other solvents. Optionally, crystallization can be effected by acidifying a soluble salt of the compound in the presence of the solvate-forming solvent.

The invention also embraces pharmaceutical compositions which include the compound of formula I, intended particularly for oral use, optionally in combination with an organic or inorganic inert carrier suitable for oral ingestion and/or other conventional additives. The pharmaceutical composition may, for instance, be in tablet, dragee, capsule form, etc., optionally enteric coated, or solutions and suspensions containing inventive compounds. The pharmaceutical composition can be produced in a known manner by a person competent within this field, by mixing the compound or formula I with the desired carrier material and/or further additives, and converting this mixture to a desired galenic form in accordance with the afore-going. Solutions and suspensions are prepared in a known manner with the aid of pharmaceutically appropriate additives. The dosage is adapted to requirements and wishes in individual situations, although dosages of 50-2000 mg/day in the case of adult patients can be mentioned as a general indication.

EXAMPLES

The identity of all final compounds have been assured by their NMR spectra and the purity by thin layer chromatography (TLC) or liquid chromatography. NMR proton spectra have been determined on a 500 MHz NMR spectrometer, with deuterated dimethylsulfoxide as solvent unless otherwise indicated. NMR chemical shift are given in ppm.

EXAMPLE 1

2-Hydroxy-5-114-1(2-pyridinylamino)sulfonyl]phenyl]ethynyl]benzoic acid

EXAMPLE 1a

Methyl 5-[(trimethylsilyl)ethynyl]-2-hydroxybenzoate

To a solution of methyl 2-hydroxy-5-iodobenzoate (275 g, 0.92 mol) in dry triethylamine (2000 ml) was added dichlorobis(triphenylphosphine)palladium (3 g, 0.004 mol) and copper(I) iodide (1.6 g, 0.008 mol). The mixture was deaerated with nitrogen. Trimethylsilylacetylene (100 g, 1.0 mol) was added with a syringe and the reaction mixture was heated to 50° C. After 30 minutes a voluminous precipitate of amine hydroiodide had formed and after 2 h the reaction was complete according to TLC. The mixture was filtered and the filtrate was evaporated in vacuo. The residue was purified by dry-flash chromatography on silica, using toluene as the eluent. Yield 211 g (92%).

EXAMPLE 1b

Methyl 5-ethynyl-2-hydroxybenzoate

A mixture of methyl 5-[(trimethylsilyl)ethynyl]-2-hydroxybenzoate (100 g, 0.57 mol) and potassium fluoride dihydrate (150 g, 1.59 mol) in DNW (600 ml) was stirred for 4 h at room temperature. The solution was extracted with ether (3×400 ml) and the combined ether extracts were washed with 1 M HCI (2×200 MI) and water (2×100 ml). The ether layer was dried with $Na_2SO_4$ and evaporated to dryness. Yield 66.5 g (93%).

EXAMPLE 1c

4-Iodo-N-(2-pyridinyl)benzenesulfoamide.

4-Iodo-benzenesulfonyl chloride, (52.3 g, 0.17 mol) was dissolved in dichloromethane (300 ml) and 2-aminopyridine (65 g, 0.69 mol) was added. The solution was stirred at room temperature for 3 days, washed with 2 M sulfinic acid (2×200 ml) and water (100 ml), dried with $Na_2SO_4$ and evaporated to dryness. Yield 46.9 g (76%).

EXAMPLE 1d

Methyl 2-hydroxy-5-[[4-[(2-pyridinylamino)sulfonyl]phenyl]ethynyl]benzoate

4-Iodo-N-(2-pyridinyl)benzenesulfonamide (35 g, 97 mmol) was dissolved in a mixture of triethylamine and tetrahydrofuran (750+750 ml). The mixture was deaerated with nitrogen and dichlorobis(triphenylphosphine)palladium (1.2 g, 1.7 mmol) and copper(I) iodide (0.6 g, 3.4 mmol) were added. Finally methyl 5-ethynyl-2-hydroxybenzoate (23 g, 130 mmol) was added. The mixture was heated to 60° C. for 4 h, evaporated to dryness. The residue was dissolved in chloroform (1000 ml) and washed with water (3×200 ml) and dried with $MgSO_4$. The solvent was evaporated in vacuo. Yield 31 g (77%). The product can be purified by flash-chromatography on silica with chloroform as the eluent.

EXAMPLE 1e

2-Hydroxy-5-[[4-[(2-pyridinylamino)sulfonyl[phenyl]ethynyl]benzoic acid

The ester from Example 1d (23.7 g, 58 mmol) was dissolved in 1 M NAOH (190 MI) and refluxed for 6 h. The cooled solution was acidified with an excess of 6 M HCI. The precipitated formed was allowed to stand for 2 h, filtered off and washed with water (3×200 ml). The white product was dried at 60° C. in vacuo. Yield 21.7 g (95 %).

$^1$H-NMR: Spin system A: δ 7.00(d), 7.66(dd), 7.95(d): (=salicylate ring), Spin system B: 5 7.66(d,2H), 7.87(d,2H): (=central benzene ring), Spin system C: δ 7.18(d), 7.73(ddd), 6.84(dd), 7.96(dd): (=pyridine ring),

EXAMPLE 2

2-Hydroxy-5-[[4-1(3-methyl-2-pyridinylamino)-sulfonyl]phenyl]ethynyl]benzoic acid

EXAMPLE 2a

4-Iodo-N-(3-methyl-2-pyridinyl)benzenesulfonamide.

This compound was prepared essentially as the corresponding compound in Example 1c. Yield 76%.

EXAMPLE 2b

Methyl 2-hydroxy-5-[[4-[(3-methyl-2-pyridinylamino)sulfonyl]phenyl]ethynyl]benzoate This compound was prepared essentially as the corresponding compound in Example 1d. Yield 76%

EXAMPLE 2c

2-Hydroxy-5-[[4-[(3-methyl-2-pyridinylamino)sulfonyl]phenyl]ethynyl]benzoic acid This compound was prepared essentially as the corresponding compound in Example 1e. Yield 24.7 g (85%)
$^1$H-NMR: Spin system A: δ7.04(d), 7.70(dd), 8.00(d): (=salicylate ring), Spin system B: δ7.70(d,2H), 7.96(d,2H): (=central benzene ring), Spin system C: δ7.66(d, broad)), 6.83(s, broad), 7.84(s, broad): (=pyridine ring), Spin system D: δ2.15(s): (=methyl group), The broadening of signals in the pyridine ring is typical for 3-methyl substituted derivatives.

EXAMPLE 3

2-Hydroxy-5-[2-[4-[(2-pyridinylamino)sulfonyl]phenyl]ethenyl]benzoic acid

EXAMPLE 3a

Methyl 5-ethenyl-2-hydroxybenzoate

Methyl 5-ethynyl-2-hydroxybenzoate (8 g, 45.4 mmol), prepared according to Example 1b, was dissolved in a mixture of diethyl ether and light petroleum (200+200 ml) in a hydrogenation flask. Quinoline (1.7 ml) and palladium on CaCO$_3$, poisoned with Pb (Lindlar catalyst; 200 mg) were added, and the flask was attached to an atmospheric pressure hydrogenation apparatus. The mixture was stirred for 2 h at room temperature, by then the calculated amount of hydrogen had been consumed. The catalyst was filtered off and the solution was evaporated to dryness. The product was purified by flash column chromatograpy on silica, using toluene as an eluent. A nearly quantitative yield was obtained.

EXAMPLE 3b

Methyl 2-hydroxy-5-[2-[4-[(2-pyridinylamino)sulfonyl]phenyl]ethenyl]benzoate 4-Iodo-N-2-pyridinylbenzenesulfonamide (25 g, 69 mmol) prepared according to Example 1c, and methyl 5-ethenyl-2-hydroxybenzoate (13.5 g, 76 mmol) were dissolved in a mixture of triethylamine and tetrahydrofuran (150+800 ml). The mixture was heated to 80° for 18 h. Palladium(II) acetate (in a total of 0.5 g) was added in small portions during the whole reaction time. The amine hydroiodide formed was filtered off and the filtrate was evaporated to dryness. The residue was dissolved in chloroform (500 ml) and purified by flashchromatography on silica with chloroform as the eluent. The solvent was evaporated in vacuo and the residue was dissolved in the smallest possible amount of hot tetrahydrofuran. The product was precipitated by addition of diethyl eter. Yield 13.5 g (47%).

EXAMPLE 3c

2-Hydroxy-5-[2-[4-[(2-pyridinylamino)sulfonyl]phenyl]ethenyl]benzoic acid

Methyl 2-hydroxy-5-[2-[4-[(2-pyridinylamino)sulfonyl]phenyl]ethenyl]benzoate (12 g, 29 mmol) was dissolved in 1 M KOH (120 ml) and the solution was refluxed for 7 h. The cooled solution was acidified with an excess of 1 M hydrochloric acid. The precipitate was filtered off and washed with water (3×200 ml). The product was redissolved in a small portion of 1 M NAOH. Water and dioxane (500+500 ml) was added and the solution was heated to 100° C. The solution was acidified with an excess of 1 M HCl, and the product precipitated upon cooling. Yield 9 g (75%).

$^1$H-NMR: Spin system A: δ7.02(d), 7.84(dd), 8.04(d): (=salicylate ring), Spin system B: δ7.73(d,2H), 7.88(d,2H): (=central benzene ring), Spin system C: δ7.22(d), 7.74(m), 6.89(ddd), 8.04(m): (=pyridine ring) Spin system D: δ7.19(d), 7.38(d): (=ethenediyl bridge).

EXAMPLE 4

2-Hydroxy-5-[2-[4-[(3-methyl-2-pyridinylamino)sulfonyl]phenyl]ethenyl]benzoic acid

EXAMPLE 4a

Methyl 2-hydroxy-5-[2-[4-[(3-methyl-2-pyridinylamino)-sulfonyl]phenyl]-ethenyl]benzoate This compound was prepared analogously to Example 3 from 4-iodo-N-(3-methyl-2-pyridinyl)-benzenesulfonamide, prepared according to Example 2a, and methyl 5-ethenyl-2-hydroxybenzoate prepared according to Example 3a. Yield 52%.

EXAMPLE 4b

2-Hydroxy-5-[2-[4-[(3-methyl-2-pyridinylamino)suphonyl]phenyl]ethenyl]benzoic acid This compound was prepared analogously to Example 3. Yield 82

$^1$H-NMR. Spin system A: δ7.02(d), 7.85(dd), 8.04(d): (=salicylate ring). Spin system B: δ7.74(d,2H), 7.92(d,2H): (=central benzene ring) Spin system C: δ7.63(d, broad), 6.8 1 (broad), 7.85 (broad): (=pyridine ring) Spin system D: δ7.21(d), 7.39(d): (=ethenediyl bridge), Spin system E: δ2.15(s): (=methyl group).

The broadening of signals in the pyridine ring is typical for 3-methyl substuted derivatives.

EXAMPLE 5

Isobutyl 2-hydroxy-5-[2-[4-[(2-pyridinylamino)sulfonyl]phenyl]ethenyl]benzoate

EXAMPLE 5a

Isobutyl 2-hydroxy-5-iodobenzoate 2-hydroxy-5-iodobenzoic acid (477 g, 1.8 mol), isobutanol (225 g), conc sulfuric acid ( 20 ml) in toluene (2 l) was refluxed for 6 h using a water separator. The solution was cooled and washed with water. The solution was treated with decolorizing carbon and the toluene was evaporated. The residue was recrystallized from methanol. Yield 376 g.

EXAMPLE 5b

Isobutyl 5-ethenyl-2-hydroxybenzoate,

Isobutyl 2-hydroxy-5-iodobenzoate (16 g, 0.05 mol), tributylamine (13.9 g, 0.075 mol), and palladium(III) acetate (0.11 g, 0.5 mmol) were dissolved in dimethylacetamide (100 ml) and the solution was charged into a 250 ml pressure-reactor.

Air was expelled by inlet of argon at 10 bar followed by venting to ambient pressure. This procedure was repeated twice. The temperature was increased to 90° C. Ethene at 13 bar was let in. After stirring for 5 min the gas was vented and the ethene-pressure was again raised to 13 bar. The temperature was increased to 110° C. during 30 min with vigorous sniffing and continous inlet of ethene to keep the pressure constant at 13 bar. After 1.5 h the temperature was decreased to 20° C. and the ethene was removed by means of argon inlet.

The solvent was evaporated at 70° C. Water (150 ml) was added. The pH was adjusted to about 5 with hydrochloric acid and the solution was extracted with toluene (2×50 ml). After reextraction with dilute sodium hydrogencarbonate (50 ml) the combined toluene extracts were evaporated to leave the product as an oil. Distillation at 0.5 mm Hg and 100°-105° C. afforded 15.4 g (70%) of chromatographically pure material. During distillation the material was protected from polymerisation by addition of 10 mg of hydroquinone.

EXAMPLE 5c

Isobutyl 2-hydroxy-5-[2-[4-[(2-pyridinylamino)sulfonyl]phenyl]ethenyl]benzoate

Palladium (II) acetate (0.15 g, 0.67 mmol) was added to a stirred solution of isobutyl 5-ethenyl-2-hydroxybenzoate (6.6g, 30 mmol) and 4-iodo-N-2-pyridinylbenzenesulfonamide (10.8 g, 30 mmol) in dimethylacetamide (40ml) and tributylamine (10 ml, 42 mmol) at 95° C. After 100 min. the solution was filtered and evaporated at 50°-60° C. (bath temp.) until solid material appeared. The mixture was diluted with isopropanol (0.5 l) and chilled in a freezer. The product was filtered off to yield 7.1 g (52%).

$^1$H-NMR. Spin system A: $\delta$7.0(d), 7.84(dd), 7.93(d): (=salicylate ring). Spin system B: $\delta$7.70(d,2H), 7.84(d,2H): (=central benzene ring), Spin system C: $\delta$7.18(d), 7.69(ddd), 6.85(ddd), 8.0(dd): (=pyridine ring) Spin system D: $\delta$7.12(d), 7.36(d): (=ethenediyl bridge) Spin system E: $\delta$1.0(d, 6H), 2.1 (m, 1H), 4.1 (d,2H): (=isobutyl group).

EXAMPLE 6

2-Hydroxy-5-[2-[4-[(2-pyridinylamino)sulfonyl[phenyl]ethenyl]benzoic acid

EXAMPLE 6a

Isopropyl 2-hydroxy-5-iodobenzoate

2-Hydroxy-5-iodobenzoic acid (I 84 g, 0.7 mol), isopropanol (50 ml), conc sulfuric acid (5 ml) and p-toluenesulfonic acid (10 g) in toluene (1 1) was refluxed using a water separator. Portions of isopropanol was added intermittently to compensate for loss of 2-propanol by dehydration. After 24 h, the solution was cooled and washed with water. The toluene was evaporated partially. Iso-octane was added, and precipitated 2-hydroxy-5-iodobenzoic acid (106 g) filtered off. The solution was taken to dryness and the residue recrystallized from methanol. Yield 64 g, (71%), corrected for recovered starting material).

EXAMPLE 6b

Isopropyl 5-ethenyl-2-hydroxybenzoate.

Isopropyl 2-hydroxy-5-iodobenzoate (30.6 g, 0.1 mol) was dissolved in a mixture of tributylamine (27.8 g, 0.15 mol) and dimethylacetamide. After addition of palladium(III) acetate and air venting the temperature was increased to 110° C. under argon. The ethene inlet was carried out following the procedure of Example 5b.

The reaction was arrested after 1.5 h by cooling to room temperature and simultaneous venting of the ethene.

After evaporation of the solvents in vacuo at 70° C. water (100 ml) was added and pH was adjusted to about 5 with hydrochloric acid. Extraction with 2×50 ml toluene and subsequent evaporation afforded an oily raw material.

The product was distilled at 0.7 mm Hg and 95°-98° C. Yield 15.5 g (75%) of chromatographically pure material.

EXAMPLE 6c

2-Hydroxy-5-[2-[4-[(2-pyridinylamino)sulfonyl]phenyl]ethenyl]benzoic acid

Isopropyl 5-ethenyl-2-hydroxybenzoate was reacted with 4-iodo-N-(2-pyridinyl)benzenesulfonamide similarly to the procedure of Example 5c. After the reaction, the solvent was evaporated, toluene was added and the suspension filtered and washed with toluene. After drying on the filter and washing with water the material was hydrolyzed and precipitated similarly to the procedure of Example 3c. Yield 40%

NMR proved the identity with the product of Example 3.

EXAMPLE 7

2-Hydroxy-5-[2-[4-[(2-pyridinylamino)sulfonyl]phenyl]ethenyl]benzoic acid

Isobutyl 2-hydroxy-5-iodo-benzoate (16 g, 0.05 mol) was reacted with ethene as described in Example 5b The reaction mixture was cooled to 85° C. and 4-iodo-N-(2-pyridinyl)benzenesulfonamide (14.8 g, 0.0425 mol.) and palladium(II) acetate (0.11 g, 0.5 mmol) were added with stirring.

After 4 hours at 85° C., all the sulfonamide had been consumed but the reaction mixture still contained some isobutyl 5-ethenyl-2-hydroxybenzoate. A further amount of sulfonamide (2.6 g, 0.0075 mol) was added and the reaction was continued for 18 h.

After addition of acetic acid the hot mixture was poured into boiling isopropanol (450 ml). Upon cooling slowly to 4° C. the solution yielded 11.3 g of the product. A further 1.5 g was obtained by concentrating the mother liquor to about 100 ml and cooling to 4° C. Total yield 12.7 g (56%)

The material was hydrolyzed overnight in refluxing 1 M potassium hydroxide (150 ml) and the product was precipitated by addition of an excess of 1M HCI. Recrystallisation from formic acid/water (70/30) yielded after filtration and drying 8.5 g (43%) product.

NMR proved the identity with the product of Example 3.

EXAMPLE 8

Isobutyl 2-hydroxy-5-[2-[4-[(3-methyl-2-pyridinylamino)sulfonyl]phenyl]-ethenyl]benzoate 10% Palladium on charcoal (0.5g) was added to a solution of isobutyl 5-ethenyl-2-hydroxybenzoate (6.6 g, 30mmol) and 4-iodo-N-(3-methyl-2-pyridinyl)benzenesulfonamide (11.2 g, 30 mmol) in dimethylacetamide (10 ml) and tributylamine (10 ml, 42 mmol) at 110° C. After 90 min. the solution was filtered and diluted with isopropanol (0.3 l) and chilled in a freezer. The product was filtered off, dried and dissolved in boiling formic acid (100 ml). The solution was filtered and water (65 ml) was added. After cooling to refrigerator temperature the product was filtered off and dried to yield 7.2 g (51%) product $^1$H-NMR: Spin system A: $\delta$7.0 (d), 7.84(d, broad), 7.94(s, broad): (=salicylate ring). Spin system B: $\delta$7.69 (d,2H), 7.9(d,2H): (=central benzene ring), Spin system C: $\delta$7.58 (broad), 6.74(broad), 7.8-8.0(broad): (=pyridine ring) Spin system D: $\delta$7.12 (d), 7.35(d): (=ethenediyl bridge) Spin system E: $\delta$2.1 (s, broad): (=methyl group) Spin system F: $\delta$1.0 (d, 6H), 2.1 (m, obscured by methyl of spin system E), 4.1 (d,2H): (=isobutyl group).

The broadening of signals in the pyridine ring is typical for 3-methyl substituted derivatives.

EXAMPLE 9

Ethyl 2-hydroxy-5-[[4-[(3-methyl-2-pyridinylamino)sulfonyl]phenyl]ethynyl]benzoate.

EXAMPLE 9a

Ethyl 5-ethynyl-2-hydroxybenzoate

This compound was synthesized from ethyl 2-hydroxy-5-iodobenzoate analogously to the method 1a and 1b for the corresponding ethyl ester.

EXAMPLE 9b

Ethyl 2-hydroxy-5-[[4-[(3-methyl-2-pyridinylamino)sulfonyl]phenyl]ethynyl]benzoate Tetrakis(triphenylphosphine)palladium (0.29 g, 0.25 mmol) and copper(I)iodide (0.095 g, 0.5 mmol) were, added to a solution of ethyl 5-ethynyl-2-hydroxybenzoate (10.5 g, 55 mmol) and 4-iodo-N-(3-methyl-2-pyridinyl)benzenesulfonamide (18.7 g, 50 mmol) in tetrahydrofuran (75 ml) and triethylamine (75 ml) at 55° C. After 2 h the solid product was collected with filtration and washed with hydrochloric acid (1M). The material was boiled in formic acid (300 ml) for 15 nun. and filtered. Water (200 ml) was added and the product crystallized upon cooling. Yield 17.3 g (79%).

$^1$H-NMR (Pyridine-d$_5$ as solvent): Spin system A: $\delta$7.11 (d), 7.70(dd), 8.14(d): (=salicylate ring). Spin system B: $\delta$7.71 (d,2H), 8.33(d,2H): (=central benzene ring), Spin system C: $\delta$7.37 (d), 6.64(dd), 7.94(d): (=pyridine ring) Spin system D: $\delta$2.11 (s, broad): (--methyl group) Spin system E: $\delta$1.22 (t, 3H), 4.33(q, 2H): (=ethyl group).

EXAMPLE 10

2-Hydroxy-5-[[4-[(3-methyl-2-pyridinylamino)sulfonyl]phenyl]ethynyl]-benzoic acid

EXAMPLE 10a

4-(3-Hydroxy-3-methyl-1-butyn-1-yl)-N-(3-methyl-2-pyridinyl)benzenesulfonamide 4-Iodo-N-(3-methyl-2-pyridinyl)benzenesulfonamide (37.4 g, 0.1 mol) was added in portions to a mixture of triethylamine (31 ml, 0.22 mol) and dimethylacetamide (25 ml) at 60° C. Dichlorobis(triphenylphosphine)palladium (0.14 g, 0.002 mol) and CuI (0.08 g, 0.004 mol) were added under a nitrogen blanket. Finally, 2-methyl-3-butyn-2-ol (10.4 g, 0.125 mol) was added in portions during 20 minutes in order to keep the temperature of the exothermal reaction at 65°-70° C.

The mixture was stirred at 65° C. for 1 hour. Water (250 ml) was added and after cooling to room temperature a cloudy precipitate was filtered off. 85% potassium hydroxide (13.2 g 0.2 mol) dissolved in water (100 ml) was added. About 100 ml of water/triethylamine was distilled off in vacuo at 50° C. The remaining solution was extracted with isobutylmethylketone (3×30 Ml) and from the water-phase about 50 ml of isobutylmethylketone/water was evaporated at 50° C.

The volume was adjusted to 300 nil with water and ethanol (100 ml ) was added. Hydrochloric acid was catiously added dropwise at 60° C. until the pH reached 4. Upon cooling to 8° C. the product precipitated. The product was filtered off, washed with water and dried. Yield 29.6 g, (90%).

EXAMPLE 10b

4-Ethynyl-N-(3-methyl-2-pyridinyl)benzenesulfonamide 4-(3-Hydroxy-3-methyl-1-butyn-1-yl)-N-(3-methyl-2-pyridinyl)benzenesulfonamide (49.6 g 0.15 mol) and water (900 ml) was heated to about 90° C. under a nitrogen blanket. 85% potassium hydroxide (64.9 g, 1.05 mol) was added at a rate sustaining vigorous boiling. A vigorous boiling was maintained for 2 hours without reflux in order to efficiently remove the acetone formed in the reaction. Water was added to keep the volume approximately constant.

The hot solution was added to ethanol (200 ml) containing a small amount Of SO$_2$. Hydrochloric acid was added dropwise at 90° C. When an opalescence was observed, activated carbon (1.5 g) was added and the solution filtered. Continued addition of hydrochloric acid was maintained to pH 4 causing precipitation of the product.

After cooling to 8° C. the solid material was filtered off and washed with water. The product was dried at 80° C. in vacuo for 18 h. Yield 38.2 g (94%)

EXAMPLE 10c

Ethyl 2-hydroxy-5-[[4-[(3-methyl-2-pyridinylamino)sulfonyl]phenyl]ethynyl]benzoate Dichlorobis(triphenylphosphine)palladium (0.07 g, 0.1 mmol) and copper(I)iodide (0.04 g, 0.2 mmol) were added to a solution of ethyl 2-hydroxy-5-iodobenzoate (14.9 g, 50 mmol) and 4-ethynyl-N-(3-methyl-2-pyridinyl)benzenesulfonamide (14.3 g, 50 mmol) in triethylamine (10 g, 0.1 mol) and dimethylacetamide (60 ml) at 65° C. Hot ethanol was added after 1 h and then hot water (100 ml) with stirring. The solid was filtered off after cooling in the refrigerator and recrystalized from formic acid and water to yield 17.0 g (77%) product.

EXAMPLE 10d

2-Hydroxy-5-[[4-[(3-methyl-2-pyridinylamino)sulfonyl]phenyl]ethynyl]benzoic acid Ethyl 2-hydroxy-5-[[4-[(3-methyl-2-pyridinylamino)sulfonyl]phenyl]ethynyl]benzoate (15.5g, 35 mmol) was refluxed in potassium hydroxide (10 g, 0.15 mol) in water (100 ml) for 1 h. After cooling to ca 70° C., ethyl acetate (50 ml) was added and hydrochloric acid was added to reach pH 7-8. Cooling during stirring and then filration gave a solid that was disolved in acetone (100 ml) and water (100 ml). The solution was acidified at ca 50° C. and cooled, filtered and washed with water. Yield 8.0 g (56%).

NMR proved the identity with the product of Example 2.

EXAMPLE 11

Potassium 2-hydroxy-5-[[4-[(3-methyl-2-pydrinylamino)sulfonyl]phenyl]ethynyl]benzoate

EXAMPLE 11a 4-(3-Hydroxy-3-methyl-1-butyn-]-yl)-N-(3-methyl-2-pyridinyl)-benzenesulfonamide The synthesis was performed as in Example 10a in 0.2 mole scale with acetone (100 ml) instead of dimethylacetamide as solvent. The reaction time at reflux (60°-62° C.) was 2 h. Yield 60.0 g, 91%.

EXAMPLE 11b

4-Ethynyl-N-(3-methyl-2-pyridinyl)benzenesulfonamide

This synthesis was run exactly as in Example 10b.

EXAMPLE 11c

Ethyl 2-hydroxy-5-[[4-[(3-methyl-2-pyridinylamino)sulfonyl]phenyl]ethynyl]-benzoate The synthesis was carried out as in Example 10c, except that hydrochloric acid was added after the ethanol and water addition. Yield 72%.

EXAMPLE 11d

Potassium 2-hydroxy-5-[[4-[(3-methyl-2-pyridinylamino)sulfonyl]phenyl]ethynyl]benzoate Ethyl 2-hydroxy-5-[[4-[(3-methyl-2-pyridinylamino)sulfonyl]phenyl]ethynyl]benzoate (15.5g, 35 mmol) was refluxed in potassium hydroxide (10 g, 0.15 mol) in water (100 ml) for I h. After cooling to ca 70° C., ethyl acetate (50 ml) was added and hydrochloric acid was added to reach pH 7-8. Cooling with sniffing and then filtration gave directly 8.5 g of the product (51%).

The corresponding acid of the product proved to be identical with the product of Example 2.

EXAMPLE 12

2-Hydroxy-5-[2-[4-[(3-methyl-2-pyridinylamino)sulfonyl]phenyl]ethenyl]benzoic acid

EXAMPLE 12a 4-(2-Bromoethyl)-N-(3-methyl-2-pyridinyl)benzenesulfonamide

3-Methyl-2-pyridinamine (431 g, 4.0 mol) was dissolved in dichloromethane (700 ml) and 4-(2-bromoethyl)benzenesulfonyl chloride (340 g, 1.33 mol) was added at room temperature. After 1 h at 20° C., the solution was heated to 35° C. for 2 h. Excess dilute hydrochloric acid was added and the phases separated. After washing once with water, the organic phase was dried with MgSO$_4$ and treated with decolorizing carbon. The solvent was evaporated and warm methanol added to the residue, which crystallized. The material was collected and recrystallized from toluene. Yield 178 g. A further crop of 36 g was obtained by workup of the mother liquor. Total yield 45%.

EXAMPLE 12b

4-Ethenyl-N-(3-methyl-2-pyridinyl)benzenesulfonamide 4-(2-Bromoethyl)-N-(3-methyl-2-pyridinyl)benzenesulfonamide (183 g, 0.5 mol) and potassium hydroxide (120 g, 1.83 mol) and hydroquinone (1 g) in ethanol (2 l) was refluxed for 1 h. 5 l water was added and the solution acidified with acetic acid. The precipitated product was collected by filtration, washed with water and dried. Yield 137 g (quantitative).

EXAMPLE 12c

Isobutyl 2-hydroxy-5-[2-[4-[(3-methyl-2-pyridinylamino)sulfonyl]phenyl]-ethenyl]benzoate Isobutyl 2-hydroxy-5-iodobenzoate (70.2 g, 0.22 mol) and 4-ethenyl-N-(3-methyl-2-pyridinyl)benzenesulfonamide (54.8 g, 0.20 mol) were suspended in a solution of tributylamine (55.5 g, 0.3 mmol) and palladium(II) acetate (0.44 g 0.0022 mol) in dimethylacetamide (200 ml)

The mixture was heated to 100° C. for 3 h. Activated carbon (2 g) was added and the suspension filtered and the filtrate poured into boiling isopropanol.

The solution was slowly cooled to 10° C. and the crystals were filtered off. The filter cake was washed with cold isopropanol (20 ml) and the product was dried. Yield 78 g, (83%).

EXAMPLE 12d

2-Hydroxy-5-[2-[4-[(3-methyl-2-pyridinylamino)sulfonyl]phenyl]ethenyl]benzoic acid The product from Example 12c (78 g) was added to a solution of potassium hydroxide (50 g, 0.78 mol) in water (600 mi) and the mixture was refluxed overnight. After addition of activated carbon (2 g) and sodium sulfite (0.5 g) the mixture was allowed to cool, with s&%g to room temperature and then filtered.

After filtration, ethanol (600 ml) was added and the solution was heated to about 90° C. Hydrochloric acid (80 ml) was added in one portion and after about 3 min. the product began to precipitate.

The suspension was slowly cooled to room temperature and the product was filtered off. The filter-cake was thoroughly washed with water and dried. Yield: 64 g, (78% over-all).

NMR proved the identity with the product of Example 4.

EXAMPLE 13

Isobutyl 2-hydroxy-5-[2-[4-[(2-pydrinylamino)sulfonyl[phenyl]ethenyl]benzoate

EXAMPLE 13a 4-(2-Bromoethyl)-N-(2-pyridinyl)benzenesulfonamide

This compound was synthesized analogously to Example 12a. Yield 67%

EXAMPLE 13b

4-Ethenyl-N-(2-pyridinyl)benzenesulfonamide

This compound was synthesized analogously to Example 12b. Yield 66%

EXAMPLE 13c

Isobutyl 2-hydroxy-5-[2-[4-[(2-pyridinylamino)sulfonyl]phenyl]ethenyl]benzoate

Isobutyl 2-hydroxy-5-iodobenzoate (19.2 g 0.06 mol), 4-ethenyl-N-(2-pyridinyl)benzenesulfonamide (13 g, 0.05 mol) and palladium(II) acetate (0.11 g, 0.0005 mol) were suspended in a mixture of tributylamine (13.8 g, 0.075 mol) and dimethylacetamide (50 ml).

After heating and sniffing for 160 min. at 85° C. acetic acid (5ml) was added and the hot mixture was poured into boiling isopropanol (400 ml). Upon cooling in the refrigerator a precipitate formed which was collected by filtration. The filter-cake was washed with water and isopropanol. Yield: 4.8 g, (21.2%).

NMR proved the identity with the product of Example 5.

EXAMPLE 14

2-Hydroxy-5-[2-[4-[(3-methyl-2-pyridinylamino)sulfonyl]phenyl]ethenyl]benzoic acid acetone solvate Potassium 2-hydroxy-5-[2-[4-[(3-methyl-2-pyridinylamino)sulfonyl]phenyl]ethenyl]-benzoate (28 g) was dissolved in water (160 ml) and acetone (240 ml) with heating to 50° C. Hydrochloric acid (6 Ml) was rapidly added. The product crystallized as a solvate containing about 0.14 mol acetone/mol 2-hydroxy-5-[2-[4-[(3-methyl-2-pyridinylamino)-sulfonyl]phenyl]ethenyl]benzoic acid. Yield 23.7 g.

$^1$H-NMR: Spin system A: δ7.04(d), 7.70(dd), 8.00(d): (=salicylate ring). Spin system B: δ7.70(d,2H), 7.95(d,2H): (=central benzene ring) Spin system C: δ7.66(d, broad)), 6.83(s, broad), 7.84(s, broad): (=pyridine ring). Spin system D: δ2.15(s, broad): (=methyl group) Spin system E: δ2. 1 O(s): (=acetone)

The broadening of signals in the pyridine ring is typical for 3-methyl substuted derivatives. The amount of acetone corresponds to about 0.15 equivalents.

EXAMPLE 15

2-Hydroxy-5-[2-[4-[(5-methyl-2-pyridinylamino)sulfonyl]phenyl]ethenyl]benzoic acid

EXAMPLE 15a

Tributylammonium 4-ethenyl-benzenesulfonate 4-(2-Bromoethyl)benzenesulfonyl chloride (89.1 g, 0.36 mol) and potassium hydroxide (86.2 g 1.44 mol) and hydroquinone (0.5 g) were refluxed in water 11) and ethanol (500 MI) for 3 h.

The solution was concentrated to about 1l by evaporation in vacuo and acidified with 2M sulfuric acid (about 400 ml). Tributylamine (71.5 g, 0.39 mol) was added and the solution extracted 4 times with dichloromethane (150 ml each). The combined organic phases was washed with 0.5M sulfuric acid (150 ml), dried with magnesium sulfate and taken to dryness. Yield 134.1 g, quantitative.

EXAMPLE 15b

Methyl2-hydroxy-5-[2-(4-sulfophenyl)ethenyl]benzoate potassium salt

Tributylammonium 4-ethenyl-benzenesulfonate (134 g, 0.36 mol), methyl 2-hydroxy-5-iodo-benzoate (101 g, 0.36 mol), tributylamine (101 g, 0.54 mol) were dissolved in dimethylacetamide (370 m). Palladium(H) acetate (0.8 g, 0.0036 mol) was added and the solution was heated with sniffing to 85° C. for 3 h. The suspension was filtered to remove insoluble palladium salts and the solution evaporated to dryness. The residue was dissolved in dichloromethane (500 ml). With vigorous stirring, a solution of potassium hydroxide (94 g, 1.45 mol) in water (300 ml) was quickly added. The precipitated dipotassium salt was filtered off and washed with dichloromethane and diethyl ether. After drying, the solid material was refluxed in acetic acid (200 ml) for 30 rain. After cooling to room temperature, the solids were filtered off and washed with diethyl ether. Yield 57.6 g (43%).

EXAMPLE 15c

Methyl 2 -acetyloxy-5-[2 -(4-sulfophenyl)ethenyl]benzoate potassium salt

Methyl 2-hydroxy-5-[2-(4-sulfophenyl)ethenyl]penzoate potassium salt (57.5 g, 0.15 mol), acetic acid (35 ml) and acetic anhydride (142 ml) were refluxed until the major part of the solids had dissolved, and then more acetic anhydride (142 ml) and sulfuric acid (1 ml) were added. After boiling for 1.5 h, the mixture was cooled to room temperature and diethyl ether was added to complete precipitation. After filtration and drying, the yield was 43.4 g (69%).

EXAMPLE 15d

Methyl 2-acetyloxy-5-[2-(4-(chlorosulfonyl)phenyl)ethenyl]-benzoate

Methyl 2-acetyloxy-5-[2-(4-sulfophenyl)ethenyl]benzoate potassium salt (42.4 g, 0.104 mol) was suspended in dichloromethane. Dimethylformamide (5 ml) and thionyl chloride were added, and the mixture refluxed with sniffing for 3 h. After cooling to room temperature, water (15 ml) was added. By careful addition of 5M sodium hydroxide, the pH of the aqueous phase was adjusted to about 7. The phases were separated and the organic phase washed with water. The solution was dried (MgSO$_4$), treated with activated carbon and filtered. After evaporation of the solvent, the solid residue was recrystallized from a toluene and petroleum ether-mixture. Yield 29.3 g (71%).

EXAMPLE 15e

2-Hydroxy-5-[2-[4-[(5-methyl-2-pyridinylamino)sulfonyl]phenyl]ethenyl]benzoic acid.

Methyl 2-acetyloxy-5-[2-(4-(chlorosulfonyl)phenyl)ethenyl]benzoate (1.2 g, 0.003 mol) 2-amino-5-methylpyridine (0.39 g, 0.0036 mol) were added to dry pyridine (10 ml) and the solution stirred at room temperature over night The solvent was evaporated and the solid residue stirred with 2M sulfuric acid. After filtration, 1.33 g intermediate ester was obtained. Ibis was refluxed with sodium hydroxide (0.6 g) in water (20 ml) and ethanol (10 ml) for 5 h. After cooling and acidification with hydrochloric acid, the crystalline precipitate was filtered off and washed with water. After stirring with hot water for 1 h, the material was collected and dried. The material was recrystallized by dissolution dissolution in hot 70% ethanol with 3 equivalents of sodium hydroxide, followed by acidification by hydrochloric acid. After filtration, washing with water, and drying the yield was 0.7 g, (58%).

$^1$H-NMR: Spin system A: δ7.01 (d), 7.8 3(dd), 8.0 1 (d): (=salicylate ring). Spin system B: δ7.72(d,2H), 7.82(d,2H): (=central benzene ring), Spin system C: δ7.11 (d), 7.56(dd), 7.68(d): (=pyridine ring) Spin system D: δ7.17(d), 7.37(d): (=ethenediyl bridge) Spin system E: δ2.15(s): (=methyl group).

EXAMPLE 16

2-Hydroxy-5-[2-[4-[[3-(phenylmethoxy)-2-pyridinylamino]sulfonyl]phenyl]ethenyl]benzoic acid This compound was synthesized analogously to Example 15e. Yield 53%

$^1$H-NMR: Spin system A: δ 6.99(d), 7.82(dd), 8.0(d): (=salicylate ring), Spin system B: δ 7.71 (d,2H), 7.93(d,2H): (=central benzene ring), Spin system C: δ 6.9(broad), 7.3(broad), 7.66(d): (=pyridine ring), Spin system D: δ 7.17(d), 7.38(d): (=ethenediyl bridge), Spin system E: δ 7.48(s), 7.3–7.4(m): (=phenyl group), Spin system F: δ 5.15(s): (=methylene group).

EXAMPLE 17

5-[2-[4-[(5-Chloro-2-pyridinylamino)sulfonyl]phenyl]ethenyl]-2-hydroxybenzoic acid This compound was synthesized analogously to Example 15e. Yield 82%

$^1$H-NMR: Spin system A: δ 7.02(d), 7.84(dd), 8.04(d): (=salicylate zing), Spin system B: δ 7.77(d,2H), 7.91(d,2H): (=central benzene ring), Spin system C: δ 7.14(d), 7.8 1 (dd), 8.24(d): (=pyridine ring), Spin system D: δ 7.20(d), 7.41(d): (=ethenediyl bridge).

EXAMPLE 18

2-Hydroxy-5-[2-[4-[(5-methyl-3-isoxazolyl)aminosulfonyl]phenyl]ethenyl]benzoic acid This compound was synthesized analogously to Example 15e. Yield 78%.

$^1$H-NMR: Spin system A: δ 7.03(d), 7.85(dd), 8.05(d): (=salicylate ring), Spin system B: δ 7.80(d,2H), 7.85(d,2H): (=central benzene ring), Spin system C: δ 6.18(s),: (=isoxazole ring), Spin system D: δ 7.21(d), 7.43(d): (=ethenediyl bridge), Spin system E: δ 2.33(s): (=methyl group).

EXAMPLE 19

2-Hydroxy-5-[2-[4-[(4-methyl-2-pyrimidyl)amino-sulfonyl]phenyl]ethenyl]benzoic acid ethanol solvate (2:1)

This compound was synthesized analogously to Example 15e. Yield 38%

$^1$H-NMR: Spin system A: δ 7.02(d), 7.84(dd), 8.03(d): (=salicylate ring), Spin system B: δ 7.76(d,2H), 7.97(d,2H): (=central benzene ring), Spin system C: δ 7.20(d), 7.40(dd): (=pyrimidine ring), Spin system D: δ 7.20(d), 7.40(d): (=ethenediyl bridge), Spin system E: δ 8 2.30(s): (=methyl group), Spin system F: δ 1.05(t, 0.5×3H), 3.42(d,0.5×2H): (ethanol).

EXAMPLE 20

2-Hydroxy-5-[2-[4-[(2-pyazinyl)aminosulfonyl]phenyl]ethenyl]benzoic acid

This compound was synthesized analogously to Example 15e. Yield 67%

$^1$H-NMR: Spin system A: δ 7.02(d), 7.84(dd), 8.03(d): (=salicylate ring), Spin system B: δ 7.78(d,2H), 7.93(d,2H): (=central benzene ring), Spin system C: δ 8.24(s, 2H), 8.40(s): (=pyrazine ring), Spin system D: δ 7.20(d), 7.41(d): (=ethenediyl bridge).

EXAMPLE 21

2-Hydroxy-5-[2-[4-[[6-fluoro-(2-benzo[d]thiazolyl)-]aminosulfonyl]phenyl]ethenyl]benzoic acid This compound was synthesized analogously to Example 15e. Yield 27%.

$^1$H-NMR: Spin system A: δ 7.0(d), 7.85(dd), 8.02(d): (=salicylate ring), Spin system B: δ 7.76(d,2H), 7.83(d,2H): (=central benzene ring), Spin system C: δ 7.77(dd), 7.25(ddd), 7.30(dd): (=benzothiazole ring), Spin system D: δ 7.20(d), 7.38(d): (=ethenediyl bridge).

EXAMPLE 22

2-Hydroxy-5-[2-[4-[N-methyl-(2-pyridinyl)aminosulfonyl]phenyl]ethenyl]benzoic acid This compound was synthesized analogously to Example 15e. Yield 81%.

$^1$H-NMR: Spin system A: δ 7.02(d), 7.87(dd), 8.04(d): (=salicylate ring), Spin system B: δ 7.56(d,2H), 7.73(d,2H): (=central benzene ring), Spin system C: δ 7.59(d), 7.85(ddd), 7.25(dd), 8.32(dd): (=pyridine ring), Spin system D: δ 7.20(d), 7.42(d): (=ethenediyl bridge), Spin system E: δ 3.2(s): (=methyl group).

EXAMPLE 23

2-Hydroxy-5-[2-[4-[(2-pyridinylamino)sulfonyl]phenyl]ethenyl]benzoic acid

EXAMPLE 23a

Isobutyl 2-hydroxy-5-[2-(4-sulfophenyl)ethenyl]benzoate dipotassium salt

Tributylammonium 4-ethenyl-benzenesulfonate (55.2 g, 0.15 mol), isobutyl 2-hydroxy-5-iodo-benzoate (47.8 g, 0.36 mol), tributylamine (41.4 g, 0.15 mol) were dissolved in dimethylacetamide (150 ml). Palladium(II) acetate (0.33 g, 0.0015 mol) was added and the solution was heated with sniffing to 85° C. for 7 h. About 3 h a further portion of isobutyl 2-hydroxy-5-iodo-benzoate (23.9 g, 0.18 mol) was added. The reaction mixture was evaporated to dryness. The residue was dissolved in dichloromethane (750 ml). With vigorous stirring, a solution of 0.5M potassium hydroxide (600 ml) was quickly added. The precipitated dipotassium salt was filtered off and washed with dichloromethane. Yield 42 g, (68%)

EXAMPLE 23b

Isobutyl 2-acetyloxy-5-[2-(4-sulfophenyl)ethenyl]benzoate potassium salt

Isobutyl 2-hydroxy-5-[2-(4-sulfophenyl)ethenyl]benzoate dipotassium salt (37.2 g, 0.09 mol) was added to a boiling solution of acetic acid (20 ml) and acetic anhydride (80 ml). Sulfuric acid (8 ml) was added cautiously and the mixture refluxed until the major part of the solids had dissolved, and then more acetic anhydride (80 ml) was added. After boiling for 1 h, the mixture was cooled to room temperature. Diethyl ether (350 ml) was added and the suspension filtered and washed with diethyl ether. Yield 36.1 g (88%)

EXAMPLE 23c

Isobutyl 2-acetyloxy-5-[2-(4-(chlorosulfonyl)phenyl)ethenyl]-benzoate

Isobutyl 2-acetyloxy-5-[2(4-sulfophenyl)ethenyl]benzoate potassium salt (36.1 g, 0.08 mol) was suspended in dichloromethane. Dimethylformamide (20 ml) and thionyl chloride (20 ml) were added, and the mixture refluxed with stirring for 3 h. After cooling to room temperature, water (15 ml) was added. By careful addition of 5M sodium hydroxide, the pH of the aqueous phase was adjusted to about 7. The phases were separated and the organic phase washed with water. The solution was dried (MgSO$_4$), treated with activated carbon and filtered. After evaporation of the solvent, the solid residue was recrystallized from a toluene and petroleum ether mixture. Yield 19.5 g (57%).

EXAMPLE 23d

2-Hydroxy-5-[2-[4-[(2-pyridinylamino)sulfonyl]-phenyl]-ethenyl]benzoic acid

Isobutyl 2-acetyloxy-5-[2-(4-(chlorosulfonyl)phenyl)ethenyl]benzoate (1.99 g, 0.0046 mol) and 2-pyridinamine (1.3 g, 0.0138 mol) was stirred in dichloromethane (10 ml) at 45° C. for 1 h. After cooling to room temperature dichloromethane (20 ml) and 2M sulfuric acid (20 ml) were added. The precipitated solid (1.3 g) was collected and washed with water. The organic phase was taken to dryness and the residue treated with boiling methanol containing ammonia (2 ml) for 20 min. After cooling, 0.6 g was collected which was combined with the first crop. The combined material (1.9 g) was refluxed with potassium hydroxide (1 g) in water (50 ml). After acidification and filtration, the solid residue was dissolved in 70% ethanol with about 3 equivalents of potassium hydroxide at the boiling point and acidified while boiling with hydrochloric acid. After filtration and drying, the yield was 1.25 g (70%).

NMR proved the identity to the product of Example 3.

EXAMPLE 24

2-Hydroxy-5-[2-[4-[(6-methyl-2-pyridinylamino)sulfonyl]phenyl]ethenyl]benzoic acid This compound was synthesized analogously to Example 23d. Yield 69%

$^1$H-NMR: Spin system A: δ 7.0(d), 7.82(dd), 8.02(d): (=salicylate ring), Spin system B: δ 7.71 (d,2H), 7.83(d,2H): (=central benzene ring), Spin system C: δ 7.04(d), 7.61 (dd), 6.66(d): (=pyridine ring), Spin system D: δ 7.17(d), 7.36(d): (=ethenediyl bridge), Spin system E: δ 2.30(s): (=methyl group).

EXAMPLE 25

2-Hydroxy-5-[2-[4-[(4-methyl-2-pyridinylamino)sulfonyl]phenyl]-ethenyl]benzoic acid ethanol solvate (2:1)

This compound was synthesized analogously to Example 23d. Yield 69%.

$^1$H-NMR: Spin system A: δ 7.0(d), 7.83(dd), 8.02(d): (=salicylate ring), Spin system B: δ 7.72(d,2H), 7.84(d,2H): (=central benzene ring), Spin system C: δ 7.04(d), 6.69(dd), 7.83(d): (=pyridine ring), Spin system D: δ 7.18(d), 7.37(d): (=ethenediyl bridge), Spin system E: δ 2.25(s): (=methyl group).

EXAMPLE 26

2-Hydroxy-5-[2-[4-[(2-pyridinylamino)sulfonyl]phenyl]ethyl]benzoic acid

A solution of 2-hydroxy-5-[2-[4-[(2-pyridinylamino)-sulfonyl]phenyl]ethenyl]benzoic acid (3 g, 7.5 mmol) in tetrahydrofuran (100 ml) and acetic acid (100 ml) was hydrogenated over palladium on charcoal (10%, 0.3 g) and hydrogen at atmospheric pressure and room temperature for 27 h. The catalyst was filtered off and the solvent was evaporated. The residue was dissolved in a solution of sodium hydroxide (0.3 g) in acetone (30 ml) and water (30 ml). The solution was acidified with hydrochloric acid at ca 50° C. After cooling, the product crystallized yielding 1.6 g (52%).

$^1$H-NMR: Spin system A: δ 6.8 1 (d), 7.29(dd), 7.61 (d): (=salicylate ring), Spin system B: δ 7.35(d,2H), 7.76(d,2H): (=central benzene ring), Spin system C: δ 7.13(d), 7.67(ddd), 6.84(ddd), 7.98(d): (=pyridine ring), Spin system D: δ 2.7–2.9(m, 4H); (=ethanediyl bridge).

EXAMPLE 27

2-Hydroxy-5-[[4-[(3-methyl-2-pyridinylamino)sulfonyl]phenyl]acetyl]benzoic acid

A solution of 2-hydroxy-5-[[4-[(3-methyl-2-pyridinylamino)sulfonyl]phenyl]ethynyl]benzoic acid (4.1 g, 0.01 mol) in formic acid (100 ml) was refluxed for 30 h. Water (200 ml) was added and the product crystallized to yield 3.0 g (71%) product.

$^1$H-NMR: Spin system A: δ 7.08(d), 8.20(dd), 8.48(d): (=salicylate ring), Spin system B: δ 7.42(d,2H), 7.90(d,2H): (=central benzene ring), Spin system C: δ 7.62(d), 6.78(broad), 7.82(broad): (=pyridine ring), Spin system D: δ 4.45(s): (=methylene bridge), Spin system E: δ 2.15(s): (=methyl group).

EXAMPLE 28

2-Hydroxy-5-[[4-[(2-pyridinylamino)sulfonyl]phenyl]acetyl]benzoic acid

The compound was prepared from 2-hydroxy-5-[[4-[(2-pyridinylamino)sulfonyl]phenyl]ethynyl]benzoic acid following the method of example 27.

$^1$H-NMR: Spin system A: δ 7.05(d), 8.14(dd), 8.44(d): (=salicylate ring), Spin system B: δ 7.38(d,2H), 7.81(d,2H): (=central benzene ring), Spin system C: δ 7.16(dd), 7.69(ddd), 6.84(ddd), 7.98(dd): (=pyridine ring), Spin system D: δ 4.4(s): (=methylene bridge).

EXAMPLE 29

2-Hydroxy-5-[1-oxo-3-[4-[(2-pyridinylamino)sulfonyl]-phenyl]-2-propenyl]benzoic acid 4-Formyl-N-(2-pyridinyl)benzenesulfonamide (5.7 g, 0.022 mol), 5-acetyl-2-hydroxybenzoic acid (6.64 g, 0.044 mol) in 5M sodium hydroxide (20 ml) were stirred for 3 days at room temperature. The solution was diluted with water (100 ml) and acetic acid added dropwise in excess. The precipitate was collected by filtration and washed with water. After drying, the material was recrystallized from acetic acid and dried at 120° C. in vacuo. Yield 6.4 g, 66%.

$^1$H-NMR: Spin system A: δ 7.12(d), 8.35(dd), 8.58(d): (=salicylate ring), Spin system B: δ 7.93(d,2H), 8.05(d,2H): (=central benzene ring), Spin system C: δ 7.23(d), 7.76(ddd), 6.88(ddd), 8.02(m): (=pyridine ring), Spin system D: δ 7.77(d), 8.02(d): (=oxopropenediyl bridge).

EXAMPLE 30

2-Hydroxy-5-[[4-[(3-methyl-2-pyridinylamino)sulfonyl]phenyl]ethynyl]-benzoic acid

EXAMPLE 30a

4-Methylphenyl 4-iodobenzenesulfonate

4-Iodobenzenesulfonyl chloride (604 g, 2 mol) was added with stirring to a solution of 4-methylphenol (227 g, 2.1 mol) and triethylamine (222 g, 2.2 mol) in toluene (1.5 l). The suspension was stirred at 60° C. for 2 h. The reaction mixture was added to excess dilute hydrochloric acid. The precipitate was filtered off and washed with ethanol. A second crop was obtained by concentrating the toluene mother liquor and collecting the solid material in the same manner. The combined crops were recrystallized from 2-propanol (2.5 l). Yield 680 g, 91%.

EXAMPLE 30b

4-Methylphenyl 4-(2-trimethylsilylethynyl)benzenesulfonate

4-Methylphenyl 4-iodobenzenesulfonate (374 g, 1 mol) was dissolved in tetrahydrofuran (1 l). Triethylamine (200 g, 2 mol), dichlorobis(triphenylphosphine)palladium (1.1 g, 1.6 mmol) and copper(I)iodide (1.9 g, 10 mmol were) added. The solution was heated to 40° C. and trimethylsilylethyne (108 g, 1.1 mol) was added during 15 min with stirring and cooling to keep the reaction temperature below 55° C. Close to the end of the addition, the colour of the reaction mixture changed from yellow to brownish green. The reaction mixture was kept at about 40° for 30 min, filtered from particulate matter and the solvent evaporated. The residue was dissolved in toluene and washed with dilute hydrochloric acid. After drying and treatment with activated carbon, the solution was evaporated. 392 g of the oily product was obtained, containing some toluene. The material was used directly in the next step without further purification.

EXAMPLE 30c

4-Methylphenyl 4-etynylbenzenesulfonate

The crude oily 4-methylphenyl 4-(2-trimethylsilylethynyl)benzenesulfonate from the preceding step (392 g) was dissolved in dimethylformamide (800 ml). Water (20 ml) and potassium fluoride (50 g, 0.86 mol) were added. The solution turned dark. After 20 min it was diluted with water and the precipitated oily product soon solidified. The material was collected and dissolved in boiling heptane (4 l). The solution was treated with activated carbon and dried with magnesium sulfate. After filtering the solution through a layer (1 cm) of alumina a crystalline product was obtained as three crops by crystallisation and evaporation. The total yield was 242 g, 89% in the two steps from 4-methylphenyl 4-iodobenzenesulfonate.

EXAMPLE 30d

Ethyl 2-hydroxy-5-[[4-(4-methylphenoxysulfonyl)phenyl]ethynyl]benzoate

Ethyl 2-hydroxy-5-iodobenzoate (58.5 g, 0.2 mol), 4-methylphenyl 4-ethynylbenzenesulfonate (54.4 g, 0.2 mol) and triethylamine (40 g, 0.4 mol) were dissolved in tetrahydrofuran (100 g).

The solution was heated to 50° C. and dichlorobis(triphenylphosphine)palladium (0.5 g, 0.72 mmol) and copper(I)iodide (1 g, 5.2 mmol) were) added simultaneously with stirring. The reaction mixture turned dark and triethylamine hydroiodide started to precipitate after about 10 min. After keeping at 45° C. for 45 min, the suspension was poured into dilute hydrochloric acid and the mixture was extracted with toluene. The toluene solution was evaporated to dryness. The residue was triturated with acetonitrile, filtered off and dried. Yield 73 g, (84%). The pooled material from several batches (270 g) was recrystallized from acetonitrile (1.2 l). Yield 250 g.

EXAMPLE 30e

Ethyl 2-hydroxy-5-[(4-sulfophenyl)ethynyl]benzoate potassium salt

Ethanol (500 ml) and toluene (100 ml) was mixed and 200 ml distilled off. Sodium metal (11.5 g, 0.5 mol) was added in portions. The sodium ethoxide solution was heated to boiling and ethyl 2-hydroxy-5-[[4-(4-methylphenoxysulfonyl)phenyl]ethynyl]benzoate (43.6 g, 0.1 mol) was added and the solution refluxed for 30 min. The solution was neutralized with acetic acid and cooled. A thick paste was formed. The solid was filtered off and washed with ethanol. It was dissolved in boiling water and potassium acetate (90 g) was added. The solution was cooled to ambient temperature and the crystalline product filtered off, washed with acetone and dried at 100° C. Yield practically quantitative. The product contains some inorganic salts.

EXAMPLE 30f

Ethyl 2-hydroxy-5-[(4-chlorosulfonylphenyl)ethynyl]benzoate

Ethyl 2-hydroxy-5-[(4-sulfophenyl)ethynyl]benzoate potassium salt (19 g, 50 mmol) was suspended in toluene (100 ml). Dimethylformamide (1 ml) and thionyl chloride (12 g) were added and the suspension was refluxed for 1 h. The reaction mixture was added to a nearly saturated sodium chloride solution and the precipitated oil was extracted with toluene. The toluene was dried and taken to dryness. The product was sufficiently pure for the next step. Yield 16 g, 88%.

EXAMPLE 30g

Ethyl 2-acetyloxy-5-[(4-chlorosulfonylphenyl)ethynyl]-benzoate

Ethyl 2-hydroxy-5-[(4-chlorosulfonylphenyl)ethynyl]benzoate (16 g, 44 mmol) was dissolved in acetic anhydride (40 ml) at 120° C. Sulfuric acid (about 0.4 ml) was added dropwise. After 5 min the solution was diluted with toluene (about 100 ml) and added to saturated sodium chloride solution with vigorous stirring. The phases were separated, the toluene solution dried and evaporated. More toluene was added and the evaporation repeated. The oily product crystallized. The product was sufficiently pure for the next step. Yield 17.0 g (95%).

EXAMPLE 30h

2-Hydroxy-5-[[4-[(3-methyl-2-pyridinylamino)sulfonyl]phenyl]ethynyl]-benzoic acid 3-methyl-2-pyridinamine (1.3 g, 12 mmol) was dissolved in dry pyridine (20 ml) and ethyl 2-acetyloxy-5-[(4-chlorosulfonylphenyl)ethynyl]-benzoate (4.1 g, 10 mmol) was added. The solution was kept at ambient temperature for 18 h. The solvent was evaporated and the residue dissolved in a small amount of tetrahydrofuran. The solution was added to a refluxing solution of potassium hydroxide (6 g) in water (100 ml) and ethanol (50 ml). After 15 min the solution was acidified with formic acid to produce a precipitate. The solid was collected by filtration, washed with water and dried. Yield 1.2 g, 29%.

NMR proved the identity with the product of Example 2.

EXAMPLE 31

2-Hydroxy-5-[[4-[[3-(phenylmethoxy)-2-pyridinylamino]sulfonyl]phenyl]ethynyl]benzoic acid This compound was synthesized analogously to Example 30h. The product was recrystallized from acetic acid and then nitromethane. Yield 58%

$^1$H-NMR: Spin system A: δ 7.06(d), 7.7(dd, overlap with other signals), 8.0(d): (=salicylate ring), Spin system B: δ 7.7(d,2H, overlap with other signals), 8.02(d,2H): (=central benzene ring), Spin system C: δ 7.40(d, broad), 6.97(t, broad), 7.7(overlap with other signals): (=pyridine ring), Spin system D: δ 7.53(d, 2H), 7.43(t, 2H), 7.36(t): (=phenyl group), pin system F: δ 5.10 (s): (=methylene group).

EXAMPLE 32

5-[[4-[(5-Chloro-2-pyridinylamino)sulfonyl]phenyl]ethynyl]-2hydroxybenzoic acid

This compound was synthesized analogously to Example 30h. The product was recrystallized twice from a dimethoxyethane/methylcyclohexane mixture. Yield 58%

$^1$H-NMR: Spin system A: δ 7.04(d), 7.70(dd), 7.99(d): (=salicylate ring), Spin system B: δ 7.73(d,2H), 7.94(d,2H): (=central benzene ring), Spin system C: δ 7.12(d), 7.82(dd), 8.23(d): (=pyridine ring).

EXAMPLE 33

2-Hydroxy-5-[[4-[(4-methyl-2-pyridinyl)amino-sulfonyl]phenyl]ethynyl]benzoic acid This compound was synthesized analogously to Example 30h. The product was dissolved in potassium hydroxide at pH about 9. Potassium acetate was added and the precipitated potassium salt was collected by filtration. The salt was dissolved in water (100 ml) and ethanol (50 ml) and the product precipitated by acidification with formic acid. Hydrochloric acid was then added to decrease the pH to less than 2. The solid was collected by filtration, washed with water and dried. Yield 2.5 g, 61%.

$^1$H-NMR: Spin system A: δ 7.04(d), 7.7(dd), 7.98(d): (=salicylate ring), Spin system B: δ 7.68(d,2H), 7.89(d,2H): (=central benzene ring), Spin system C: δ 6.70(dd), 7.07(broad), 7.82(d): (=pyridine ring), Spin system D: δ 2.24(s): (=methyl group).

EXAMPLE 34

2-Hydroxy-5-[[4-[[6-fluoro-(2-benzo[d]thiazolyl)-]aminosulfonyl]phenyl]ethynyl]benzoic acid This compound was synthesized analogously to Example 30h. The product was dissolved in dilute sodium hydroxide and carefully neutralized to about pH 7. Some solid material was filtered off and the solution reprecipitated by the addition of formic and hydrochloric acid as before. Yield 2.2g, 47%.

$^1$H-NMR: Spin system A: δ 7.03(d), 7.70(dd), 7.99(d): (=salicylate ring), Spin system B: δ 7.74(d,2H), 7.90(d,2H): (=central benzene ring), Spin system C: δ 7.79(dd), 7.27(ddd), 7.33(dd): (=benzothiazole ring).

EXAMPLE 35

2-Hydroxy-5-[[4-[N-methyl-(2-pyridinyl)aminosulfonyl]phenyl]ethynyl]benzoic acid This compound was synthesized analogously to Example 30h. Yield 2.6 g, 64%.

$^1$H-NMR: Spin system A: δ 7.05(d), 7.7(dd, overlap with other signals), 8.01(d): (=salicylate ring), Spin system B: δ 7.63 (d,2H), 7.7 1 (d,2H): (=central benzene ring), Spin system C: δ 7.58(ddd), 7.89(ddd), 7.25(ddd), 8.32(ddd): (=pyridine ring), Spin system E: δ 3.2(s): (=methyl group).

EXAMPLE 36

2-Hydroxy-5-[[4-[(5-methyl-3-isoxazolyl)aminosulfonyl]phenyl]ethynyl]benzoic acid

EXAMPLE 36a

Ethyl 2-hydroxy-5-[[4-[(5-methyl-3-isoxazolyl)aminosulfonyl]phenyl]ethynyl]-benzoate 5-methyl-2-isoxazolamine (1.2 g, 12 mmol) was dissolved in dry pyridine (20 ml) and ethyl 2-acetyloxy-5-[(4-chlorosulfonylphenyl)ethynyl]-benzoate (4.1 g, 10 mmol) was added. The solution was kept at ambient temperature for 72 h. The solvent was evaporated and the residue dissolved in a small amount of tetrahydrofuran. The solution was added to a refluxing solution of potassium hydroxide (2.5 g, 38 mmol) in water (100 ml). After 5 min, ethanol (50 ml) was added and the solution acidified with formic acid to produce a precipitate. The solid was collected by filtration, washed with water and dried. It was recrystallize three times from ethanol. Yield 1.5 g, 35%.

EXAMPLE 36b

2-Hydroxy-5-[[4-[(5-methyl-3-isoxazolyl)aminosulfonyl]phenyl]ethynyl]benzoic acid Ethyl 2-hydroxy-5-[[4-[(5-methyl-3-isoxazolyl)aminosulfonyl]phenyl]ethynyl]benzoate (1.5 g) was added to a boiling solution of potassium hydroxide (6 g, 92 mmol) in water (100 ml). After 5 min, ethanol (25 ml) was added and the solution acidified with formic acid. The precipitate was collected by filtration, washed with water and dried. Yield 1.4 g, quantitative.

$^1$H-NMR: Spin system A: $\delta$ 7.02(d), 7.68(dd), 7.97(d): (=salicylate ring), Spin system B: $\delta$ 7.74(d,2H), 7.87(d,2H): (=central benzene ring), Spin system C: $\delta$ 6.14(s), : (=isoxazole ring), Spin system E: $\delta$ 2.25(s): (=methyl group).

EXAMPLE 37

4-Fluoro-2-hydroxy-5-[2-[4-[(3-methyl-2-pyridinylamino)sulfonyl]phenyl]ethenyl]benzoic acid

EXAMPLE 37a

Ethyl4-fluoro-2-hydroxybenzoate

4-Fluoro-2-hydroxy-benzoic acid (10.8 g, 0.07 mol), sodium acetate (6.9 g, 0.084 mol), ethyl iodide (55 g, 0.35 mol) and dimethylformamide was stirred at ambient temperature for 48 h. The mixture was poured into water and extracted with n-hexane. The solution was filtered through a plug of silica gel and evaporated. The residue was almost pure product and was used directly in the next step. Yield 10.2 g, 80%.

EXAMPLE 37b

Ethyl 4-fluoro-2-hydroxy-5-iodobenzoate

Ethyl 4-fluoro-2-hydroxybenzoate (10.2 g, 55 mmol)) was dissolved in n-heptane. Iodo monochloride (12 g, 74 mmol) was added dropwise at ambient temperature with sniffing. After 1 h, water was added and then solid sodium sulfite in small portions until the suspension was decolourized. More n-heptane was added to clear solution and the phases separated. The organic phase was dried and concentrated. The product crystallized on cooling. It was collected by filtration and washed with cold n-heptane. The crude yield was 10 g. The product was a mixture of ethyl 4-fluoro-2-hydroxy-5-iodobenzoate (about 80%) and the 5 chloro analogue (about 20%).

EXAMPLE 37c

Ethyl 4-fluoro-2-hydroxy-5-[[4-[(3-methyl-2-pyridinylamino)-sulfonyl]phenyl]ethynyl]benzoate Ethyl 4-fluoro-2-hydroxy-5-iodobenzoate (3.6 g, 80%, 10 mmol), 4-ethynyl-N-(3-methyl-2-pyridinyl)-benzenesulfonamide (2.7 g, 10 mmol) and triethylamine (5 g, 50 mmol) were suspended in tetrahydrofuran (20 ml) and the mixture heated to 50° C. Dichlorobis(triphenylphosphine)palladium (45 mg, 0.06 mmol) and copper(I)iodide (76 mg, 0.4 mmol) were added with stirring. After about 15 min a practically clear solution had formed. After 3 h at 50° C. the solution was taken to dryness and triturated with isobutylmethylketone and dilute hydrochloric acid. The organic phase was separated and the solvent evaporated. The oily residue was triturated with a small amount of acetonitrile to form crystals. These were recrystallized from acetic acid. The product was dissolved in a small amount of chloroform and the solution applied on top of a short silica gel column and eluted with 25% isobutylmethylketone in toluene. The pure product resulted after evaporation of the solvent Yield 2.0 g, 44%.

EXAMPLE 37d

4-Fluoro-2-hydroxy-5-[[4-[(3-methyl-2-pyridinylamino)sulfonyl]phenyl]ethynyl]benzoic acid Ethyl 4-fluoro-2-hydroxy-5-[[4-[(3-methyl-2-pyridinylamino)-sulfonyl]phenyl]ethynyl]benzoate (2.0 g, 4.4 mmol) was added to a boiling solution of potassium hydroxide (2.0 g) in water (50 ml). After 15 min water (50 ml) and ethanol(50 ml) were added and the solution acidified with formic acid and hydrochloric acid. After cooling the precipitate was filtered off and dried. Yield quantitative.

$^1$H-NMR. (Solvent: trifluoroacetic acid) Spin system A: $\delta$ 6.80(d), 8.2 1 (d): (=salicylate ring), Spin system B: $\delta$ 7.72(d,2H), 7.91(d,2H): (=central benzene ring), Spin system C: $\delta$ 7.64(dd), 8.3 1 (d), 8.45(d): (=pyridine ring), Spin system D: $\delta$ 2.35(s): (=methyl group).

EXAMPLE 38

4-Fluoro-2-hydroxy-5-[2-[4-[(3-methyl-2-pyridinylamino)sulfonyl]phenyl]ethenyl]benzoic acid

EXAMPLE 38a

Ethyl 4-fluoro-2-hydroxy-5-[2-[4-[(3-methyl-2-pyridinylamino)-sulfonyl]phenyl]ethenyl]benzoate 4-Ethenyl-N-(3-methyl-2-pyridinyl)benzenesulfonamide (2.7 g, 10 mmol), ethyl 4-fluoro-2-hydroxy-5-iodobenzoate (3.6 g, 80%, 10 mmol), triethylamine (5 ml) and N,N-dimethylacetamide (5 ml) were mixed and heated to 50° C. Palladium acetate (40 mg) was added and the solution kept at 50° C. for 18 h. The solution was poured into water and the precipitate dissolved in chloroform. The solution was dried, applied on top of a short silica gel column and eluted with 30% isobutylmethylketone in toluene. The pure fractions were collected and evaporated to dryness. After trituration with acetonitrile the product crystallized. Yield 1.1 g.

EXAMPLE 38b

4-Fluoro-2-hydroxy-5-[2-[4-[(3-methyl-2-pyridinylamino)-sulfonyl]phenyl]ethenyl]benzoic acid Ethyl 4-fluoro-2-hydroxy-5-[2-[4-[(3-methyl-2-pyridinylamino)-sulfonyl]phenyl]ethenyl]benzoate (1.1 g, 2.4 mmol) was added to a boiling solution of potassium hydroxide (2.0 g) in water (50 ml). Ethanol (10 ml) was added to produce a clear solution. After 15 min ethanol (25 ml) were added and the solution neutralized to pH about 7 with formic acid. The slightly opalescent solution was treated with decolourizing carbon and acidified with formic acid. After cooling the precipitate was filtered off and dried. Yield 0.8 g $^1$H-NMR. (Solvent: trifluoroacetic acid) Spin system A: $\delta$ 6.79(d), 8.29(d): (=salicylate ring), Spin system B: $\delta$ 7.72(d,2H), 7.90(d,2H): (=central benzene ring), Spin system C: $\delta$ 7.62(dd), 8.29(d), 8.44(d): (=pyridine ring), Spin system D: $\delta$ 7.21(d), 7.35(d): (=ethenediyl bridge), Spin system E: $\delta$ 2.36(s): (=methyl group).

EXAMPLE 39

2-Hydroxy-5-[[3-[(3-methyl-2-pyridinylamino)sulfonyl]phenyl]ethynyl]benzoic acid

EXAMPLE 39a

3-Iodo-N-(3-methyl-2-pyridinyl)benzenesulfonamide 32.4 g 3-methyl-2-pyridinamine (32.4 g, 0.3 mol) was dissolved in isobutylmethylketone (200 ml) and 3-iodobenzenesulfonyl chloride (30.2 g, 0.1 mol) was added with stirring. The solution was kept at 40° C. for 8 h and then added to dilute hydrochloric acid. The precipitate was filtered off and the organic phase was separated and evaporated. The residue was combined with the first solid material and recrystallized from ethanol. The crystals were dissolved in 1M sodium hydroxide (about 200? ml) and extracted with isobutylmethylketone (3×100 ml). The aqueous phase was partially evaporated to remove isobutylmethylketone residues. Ethanol (100? ml) was added and the solution acidified with acetic acid. The precipitate was filtered off, washed with water and dried. Yield 23 g, 61%.

EXAMPLE 39b

Ethyl 2-hydroxy-5-[[3-[(3-methyl-2-pyridinylamino)sulfonyl]-phenyl]ethynyl]benzoate 3-Iodo-N-(3-methyl-2-pyridinyl)benzenesulfonamide (18.7 g, 50 mmol), ethyl 5-ethynyl-2-hydroxybenzoate (9.5 g, 50 mmol), triethylamine (65 ml) and tetrahydrofuran (65 ml) were stirred at 60° C. Dichlorobis(triphenylphosphine)palladium (250 mg, 0.36 mmol) and copper(I)iodide (140 mg, 0.7 mmol) were added with stirring. After 1 h the solution was poured into dilute hydrochloric acid and extracted with ethyl acetate. The organic phase was washed with water, dried, treated with activated carbon and the solvent evaporated. The residue was recrystallized from methanol, then from toluene and finally from acetic acid. Yield 12.7 g 58%.

EXAMPLE 39c cl

2-Hydroxy-5-[[3-[(3-methyl-2-pyridinylamino)sulfonyl]-phenyl]-ethynyl]benzoic acid Ethyl 2-hydroxy-5-[[3-[(3-methyl-2-pyridinylamino)-sulfonyl]-phenyl]-ethynyl]benzoate (4 g, 9.2 mmol) was added to a boiling solution of potassium hydroxide (6 g, 90 mmol) in water (100 ml). After 15 min ethanol (50 ml) was added and the solution acidified with hydrochloric acid. the product was collected by filtration and dried at 110° C. Yield 3.5 g, 93%.

$^1$H-NNR: Spin system A: δ 7.0(d), 7.68(dd), 7.97(d): (=salicylate ring), Spin system B: δ 7.55(t), 7.69(d), 7.90(d), 8.06(s): (=central benzene ring), Spin system C: δ 7.62(d, broad), 6.78(t, broad), 7.81(s, broad): (=pyridine ring), Spin system D: δ 2.10(s): (=methyl group).

The broadening of signals in the pyridine ring is typical for 3-methyl substituted derivatives.

EXAMPLE 40

Effect of Compounds on Human Lymphocyte Proliferation

Peripheral blood mononuclear cells were isolated from heparinized blood from healthy volunteers by density gradient centrifugation as described by Bain and Pshyk, Transplantation Proc, 4: 163–164 (1972). Cell proliferation induced by Concanavalin A was measured in a standard assay such as described in Söderström et al., Scand J Immunol, 32:503–516 (1990) using 5% fetal bovine serum in the culture medium. The reaction mixture (final concentrations) consisted of 200 000 cells stimulated with 2.5 μg/ml Concanavalin A and test compounds in a total volume of 0.2 ml. The test compounds were added at the start of the assay, which was run for a total of three days with addition of radioactive [3H]-thymidine during the last 18 h. Cell bound radioactivity was measured in a liquid scintillation counter.

TABLE

Inhibitory effects of 250 μM test compounds on Concanavalin A-induced proliferation of human lymphocytes. Data are from 2 experiments given as per cent inhibition of proliferation in the absence of test compounds.

| Test compound From Example | Inhibition, % Mean | S.D. |
| --- | --- | --- |
| Sulfasalazine | 53.7 | 5.2 |
| 1 | 95.6 | 2.9 |
| 2 | 99.5 | 0.2 |
| 3 | 73.6 | 21.2 |
| 4 | 92.3 | 4.6 |
| 15 | 93.9 | 2.1 |
| 16 | 95.4 | 0.7 |
| 17 | 99.5 | 0.2 |
| 18 | 43.8 | 26.9 |
| 19 | 10.3 | 11.9 |
| 20 | 34.8 | 10.2 |
| 21 | 99.8 | 0.2 |
| 22 | 99.8 | 0.1 |
| 26 | 16.0 | 11.5 |
| 27 | 37.3 | 23.4 |
| 28 | 15.0 | 13.1 |
| 29 | 66.0 | 4.7 |
| 31 | 100 | 0 |
| 32 | 100 | 0 |
| 34 | 98 | 3 |
| 35 | 99 | 2 |
| 37 | 100 | 0 |
| 38 | 100 | 0 |
| 39 | 100 | 0 |

EXAMPLE 41

Effects of Test Compounds on Superoxide Production of Human Granulocytes

Granulocytes were isolated from the heparinized blood from healthy volunteers. The superoxide assay was essentially that of J M McCord and I Fridovich (J. Biol. Chem. 244:6049–6055 (1969)) as modified by G Carlin et al. (Pharmacol. Toxicol 65:121–127 (1989)). The reaction mixture contained (final concentrations) 125 μM cytochrome C in Dulbeccos phosphate buffer with Mg and Ca, 10 μM test compound and 400 000 granulocytes treated with 5 μg/ml of cytochalasin B immediately before the experiment. This reaction mixture was preincubated at 37° C. for 10 minutes, whereafter 10 nM N-formyl-L-methionyl-L-leucyl-L-phenylalanine was added to start the reaction, making the final volume 1 ml. After 10 minutes the tubes were centrifuged and the absorbance of the supernatant at 540 and 550 nm was measured. The superoxide production was expressed as the difference in absorbance at these wavelengths.

TABLE

Inhibitory effects of 10 μM test compound on FMLP-induced superoxide production. Data are given as per cent inhibition of superoxide production in the absence of test compounds.

| Test compound From Example | Inibition, % Mean | S.D. | Number of exp. |
| --- | --- | --- | --- |
| Sulfasalazine | 63.5 | 11.8 | 19 |
| 1 | 71.0 | 13.6 | 4 |

TABLE-continued

Inhibitory effects of 10 μM test compound on FMLP-induced superoxide production. Data are given as per cent inhibition of superoxide production in the absence of test compounds.

| Test compound From Example | Inhibition, % Mean | S.D. | Number of exp. |
| --- | --- | --- | --- |
| 2 | 86.0 | 7.3 | 4 |
| 3 | 55.7 | 17.0 | 4 |
| 4 | 76.9 | 10.6 | 4 |
| 5 | 25.8 | 10.1 | 3 |
| 16 | 94.6 | 1.1 | 3 |
| 17 | 71.9 | 5.9 | 3 |
| 18 | 44.2 | 6.4 | 3 |
| 19 | 65.9 | 2.9 | 3 |
| 20 | 35.1 | 7.9 | 3 |
| 21 | 93.0 | 4.2 | 3 |
| 22 | 85.5 | 8.2 | 4 |
| 25 | 45.5 | 4.1 | 3 |
| 26 | 26.8 | 16.2 | 4 |
| 27 | 32.7 | 17.1 | 4 |
| 28 | 17.9 | 8.7 | 4 |
| 29 | 33.4 | 11.9 | 5 |

EXAMPLE 42

Effects of Test Compounds on Superoxide Production of Human Granulocytes at 100 um Concentration Granulocytes were isolated from the heparinized blood from healthy volunteers. The superoxide assay was essentially that of J M McCord and I Fridovich (J. Biol. Chem. 244:6049-6055 (1969)) as modified by G Carlin et al. (Pharmacol. Toxicol 65:121-127 (1989)). The reaction mixture contained (final concentrations) 125 μM cytochrome C in Dulbeccos phosphate buffer with Mg and Ca, 100 μM test compound and 600 000 granulocytes treated with 5 μg/ml of cytochalasin B immediately before the experiment. This reaction mixture was preincubated at 37° C. for 10 minutes, whereafter 100 nM N-formyl-L-methionyl-L-leucyl-L-phenylalanine was added to start the reaction, making the final volume 1 ml. After 10 minutes the tubes were centrifuged and the absorbance of the supernatant at 540 and 550 nm was measured. The superoxide production was expressed as the difference in absorbance at these wavelengths.

TABLE

Inhibitory effects of 100 μM test compound of FMLP-induced (100 mM) superoxide production. Data are given as per cent inhibition of superoxide production in the absence of test compounds.

| Test compound From Example | Inhibition, % Mean | S.D. | Number of exp. |
| --- | --- | --- | --- |
| Sulfasalazine | 65.4 | 9.0 | 3 |
| 2 | 94.1 | 4.2 | 3 |
| 33 | 92.1 | 3.7 | 3 |
| 37 | 97.5 | 3.2 | 3 |
| 38 | 98.7 | 1.7 | 3 |
| 39 | 93.5 | 1.8 | 3 |

From the results of Examples 40 to 42 the compounds of Examples 2, 16, 17, 21, 22, 33, 37, 38 and 39 should be the most active of which the compound of Example 2 is at the present stage considered to be the best one.

We claim:

1. A compound of the formula Het—NR—$SO_2$—$Ph^1$—$APh^2$(COOH)(OH) and tautomeric forms, salt, solvate, $C_{1-6}$- alkyl ester and pharmaceutical composition of the compound, in which compound $Ph^1$ and $Ph^2$ are optionally substituted benzene rings with the condition that carboxy and hydroxy are ortho to one another, A is a bridge and Het is $(R_1,R_2,R_3)$—Het' wherein Het'— is the heterocyclic ring and satisfies the formula:

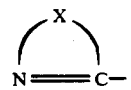

where the free valency binds to NR, and X is (i) —N=CH—NH—, —N=CH—S, —N=CH—O—, —NH—N=CH—, —O—CH=CH—, —CH=CH—O—, —NH—CH=CH—, —CH=CH—NH—, —CH=CH—S—, —CH=N—NH, (ii) —CH=CH—CH=CH—, —CH=CH—CH=N, —CH=N—CH=CH, —CH=CH—N=CH—, —N=CH—CH=CH—, where mutually adjacent bold-typed hydrogen atoms (H) can be substituted in pairs with —CH=CH—CH=CH—, so as to form a bicyclic structure (condensed rings); and $R_1$, $R_2$ and $R_3$ are substituents on carbon atoms in Het' and are chosen from among the group hydrogen, lower alkyl, halogen, hydroxy, cyano, carboxy, lower alkoxy, benzyloxy, lower acyl (including acetyl and benzoyl) and phenyl and benzyl, wherein any occurrent benzene rings can be substituted, A is a bridge which is stable against reduction because it is not azo; and R is hydrogen or lower alkyl.

2. The compound according to claim 1, characterized in that A and $SO_2$ bind para or meta to one another on $Ph^1$ and that hydroxy and A bind para to one another on $Ph^2$.

3. The compound according to claim 1, characterized in that —A— is a straight carbon chain having at most three carbon atoms including one C—C—, C=C— or C≡C-bond, optionally together with a carbonyl (C=O).

4. The compound according to claim 1, characterized in that —A— is chosen from among —C≡C—, —C=CH—, —$CH_2$—$CH_2$—, —CO—CH=CH—, —CH=CH—CO— and —$CH_2$—CO—, when applicable in the trans-form.

5. The compound according to claim 1, characterized in that —A— is chosen from among —C≡C— and —CH=CH—.

6. The compound according to claim 1, characterized in that R is hydrogen.

7. The compound according to claim 1, characterized in that R is lower alkyl.

8. The compound according to claim 1, characterized in that X is: —O—CH=CH—, —N—CH=CH—, —CH=CH—NH—, and —CH=CH—S—.

9. The compound according to claim 1, characterized in that X is: —CH=CH—CH=CH—, —CH=N—CH—CH—, —CH=CH—N=CH— and —N=CH—CH=CH—.

10. The compound according to claim 1, characterized in that Het' is a monocyclic structure.

11. The compound according to claim 1, characterized in that Het' is a bicyclic structure.

12. The compound according to claim 1, characterized in that $R_1$ and $R_2$ are hydrogen and $R_3$ is chosen from among remaining substituents.

13. The compound according to claim 12, characterized in that $R_3$ is hydrogen.

14. The compound according to claim 1, characterized in that Het' is pyridine.

15. The compound according to claim 14, characterized in that A is —C≡C— or —CH=CH—, and in that $R_3$ is not hydrogen.

16. The compound according to claim 15, characterized in that R is hydrogen.

17. The compound according to claim 15, characterized in that $R_3$ is ortho to the —NRSO$_2$— substituent in the pyridine ring.

18. The compound of claim 4, wherein —CH=CH—, —CH=CH—CO— and —CO—CH=CH— are in transform.

19. The compound according to claim 7, wherein R is methyl.

20. The compound according to claim 14, wherein $R_3$ is methyl.

* * * * *